(12) United States Patent
Chang

(10) Patent No.: US 7,732,580 B2
(45) Date of Patent: Jun. 8, 2010

(54) **COMPOSITIONS FOR ELICITING AN IMMUNE RESPONSE AGAINST *MYCOBACTERIUM AVIUM* SUBSPECIES *PARATUBERCULOSIS***

(75) Inventor: Yung-Fu Chang, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/248,764

(22) Filed: Oct. 9, 2008

(65) Prior Publication Data

US 2009/0099083 A1    Apr. 16, 2009

Related U.S. Application Data

(60) Provisional application No. 61/094,552, filed on Sep. 5, 2008, provisional application No. 60/979,822, filed on Oct. 13, 2007.

(51) Int. Cl.
*A61K 38/16*    (2006.01)
*C07K 14/00*    (2006.01)

(52) U.S. Cl. .................. 530/402; 530/350; 514/12; 424/248.1

(58) Field of Classification Search ............... None
See application file for complete search history.

(56) References Cited

U.S. PATENT DOCUMENTS 7,074,559 B2    7/2006    Kapur et al.
2007/0042383 A1 *    2/2007    Kapur et al. .................. 435/6

2007/0134274 A1    6/2007    Talaat

FOREIGN PATENT DOCUMENTS

WO    2006/089043    *    8/2006
WO    WO-2006089043 A2    8/2006
WO    WO-2006089043 A3    4/2007

OTHER PUBLICATIONS

Chen,Li et al, Vaccine, 2008, vol. 26, pp. 1253-1262, Immune reponses in mice to *Mycobacterium avium* subsp. paratuberculosis following vaccination with a novel 74F recombinant polyprotein.*
Buergelt C.D. et al., Nested Polymerase Chain Reaction and Prenatal Detection of *Mycobacterium avium* Subspecies paratuberculosis (Map) in Bovine Allantoic Fluid and Fetuses. International Journal of Applied Research in Veterinary Medicine. 2006, vol. 4, No. 3, pp. 232-238.

(Continued)

*Primary Examiner*—Robert B Mondesi
*Assistant Examiner*—Ginny Portner
(74) *Attorney, Agent, or Firm*—Marjama Muldoon Blasiak & Sullivan LLP

(57)    ABSTRACT

Provided are compositions and methods for stimulating an immune response against *Mycobacterium avium* subspecies *paratuberculosis* (MAP). The compositions include a recombinant polypeptide that contains from its N-terminus to C-terminus a C-terminal fragment of MAP protein Map3527, a Map1519 protein amino acid sequence, followed by an N-terminal portion of Map3527. The method comprises administering the composition to an animal in an amount effective to stimulate an immunological response against MAP bacteria. The method is of benefit to any animal susceptible to MAP infection, but is particularly beneficial for ruminants.

18 Claims, 22 Drawing Sheets

OTHER PUBLICATIONS

Figure 1A:
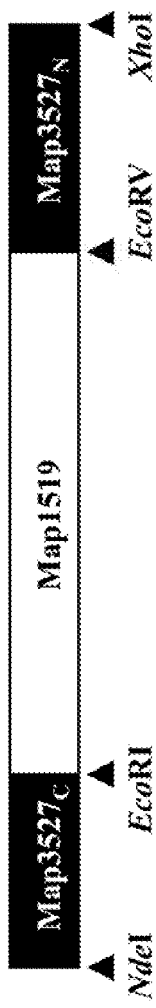

Dheenadhayalan V. et al. Cloning and characterization of the genes coding for antigen 85A, 85B and 85C of *Mycobacterium avium* subsp. paratuberculosis. DNA Sequence, 2002; 13(5):287-294.

Kalis C. H. et al. Use of long-term vaccination with a killed vaccine to prevent fecal shedding of *Mycobacterium avium* subsp paratuberculosis in dairy herds. Am J Vet Res 2001;62(2):270-4.

Koets A.P. et al., Genetic variation of susceptibility to *Mycobacterium avium* subsp. paratuberculosis infection in dairy cattle. J Dairy Sci 2000;83(11):2702-8.

Kormendy B. Paratuberculosis vaccine in a large dairy herd. Acta Vet Hung 1992;40(3):171-84.

Li L. et al., The complete genome sequence of *Mycobacterium avium* subspecies paratuberculosis. Proceedings National Academy Sciences (USA). Aug. 30, 2005, vol. 102, No. 35, pp. 12344-12349 and GenBank Accession No: AE016958.

Mullerad J. et al. The immunogenicity of *Mycobacterium paratuberculosis* 85B antigen. Med. Microbiol. Immunol. 2002; 190:179-187.

PCT/US/08/79425 International Search Report. Jan. 14, 2009. 3 pp.

Sechi L.A., et al. Immunogenicity and cytoadherence of recombinant heparin binding haemagglutinin (HBHA) of *Mycobacterium avium* subsp. paratuberculosis: Functional promiscuity or a role in virulence? Vaccine 2006;24(3):236-243.

Shin S.J. et al. Comparative antibody response of five recombinant antigens in related to bacterial shedding levels and development of serological diagnosis based on 35 kDa antigen for *Mycobacterium avium* subsp. paratuberculosis, J. Vet. Sci. 2004; 5(2), 111-117.

Shin S.J. et al. In vitro cellular immune responses to recombinant antigens of *Mycobacterium avium* subsp. paratuberculosis. Infect Immun 2005;73(8):5074-85.

Uzonna J.E. et al. Efficacy of commercial and field-strain *Mycobacterium paratuberculosis* vaccinations with recombinant IL-12 in a bovine experimental infection model. Vaccine 2003, vol. 21, pp. 3101-3109.

* cited by examiner

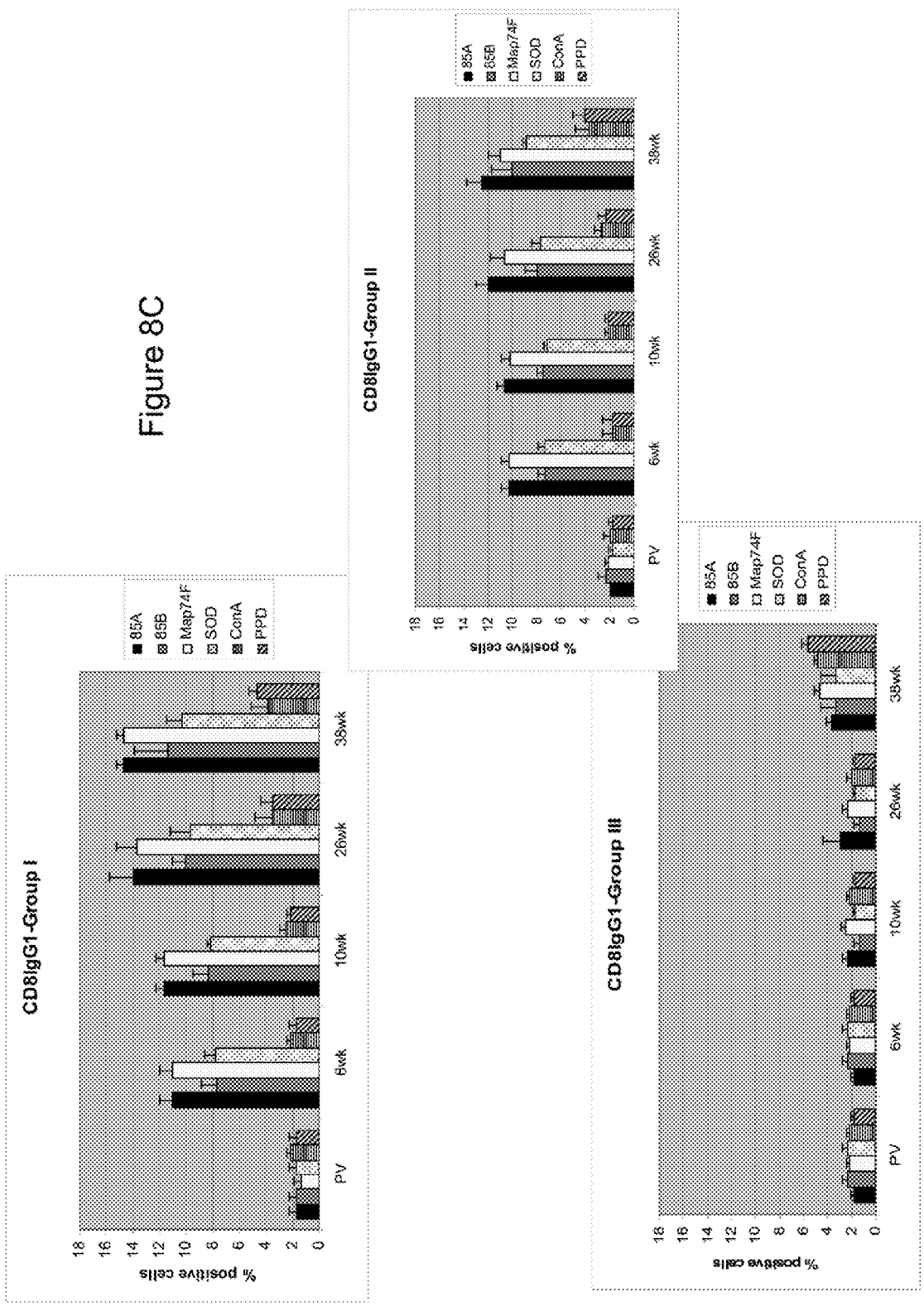

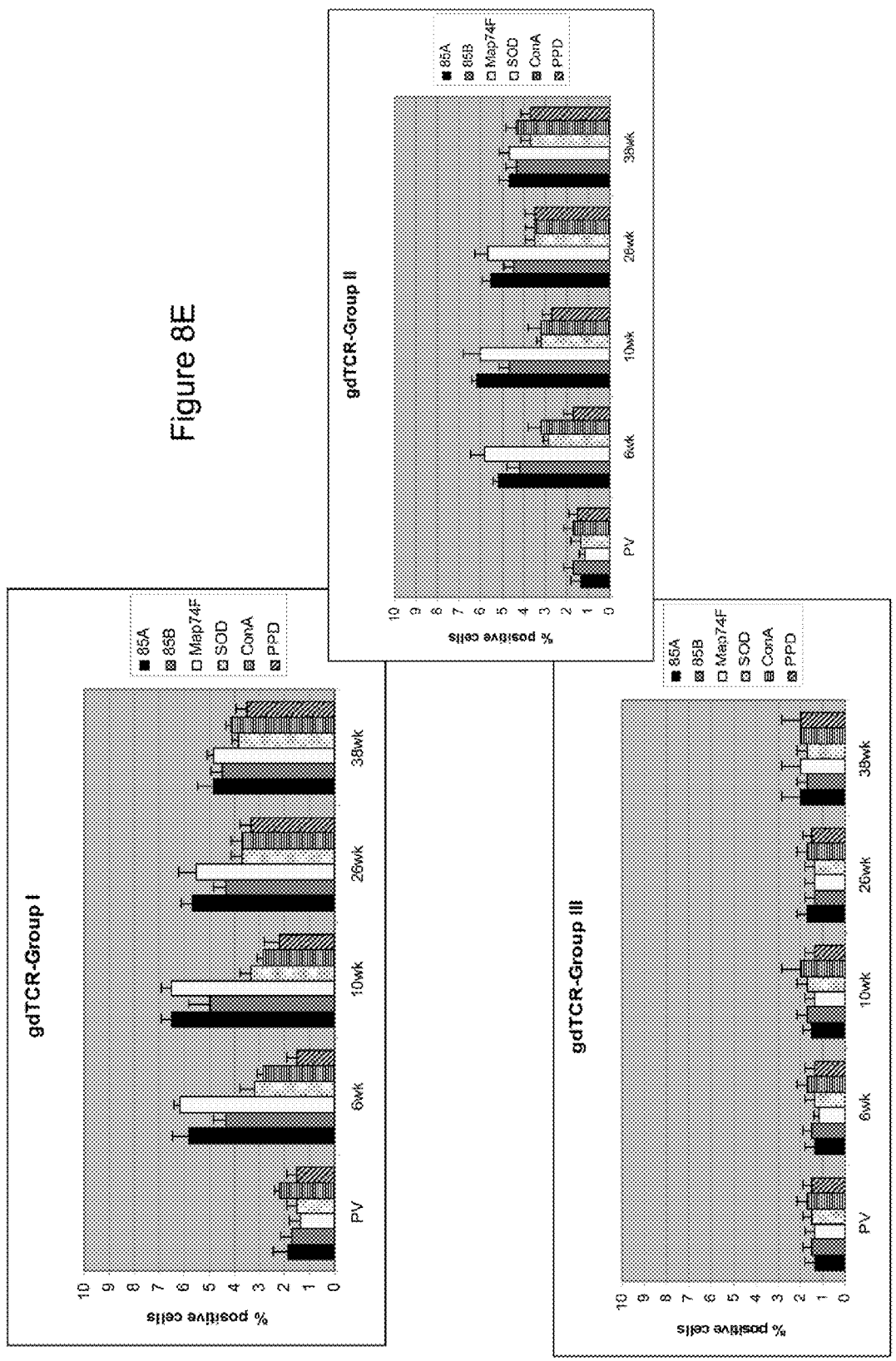

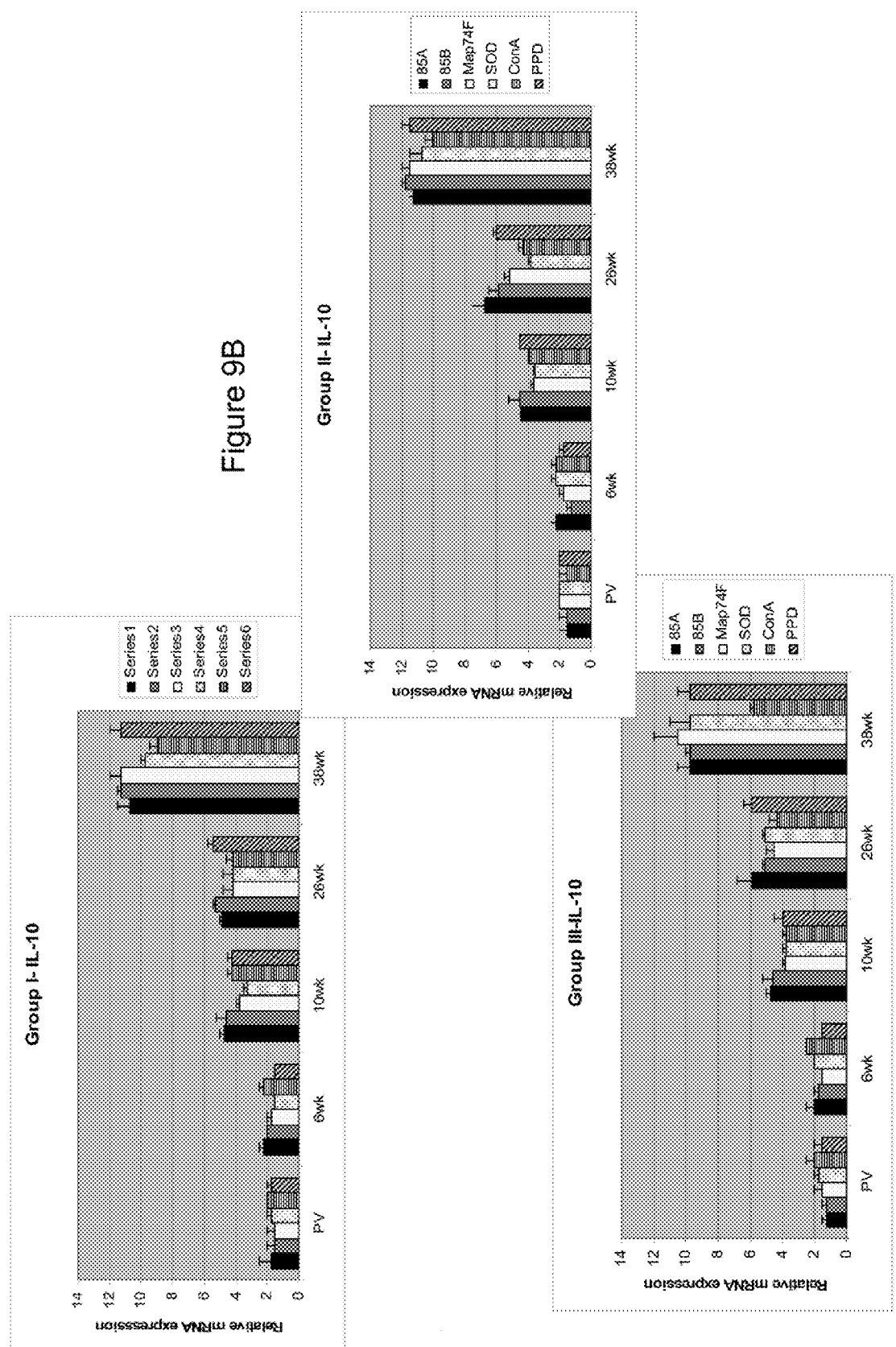

Figure 11

| Group | Animal # | S | T | ML1 | ML2 | ML3 | MRL | ICL | HL | Da | Dd | J1 | J2 | J3 | IP1 | IP2 | IM1 | IM2 | ID1 | ID2 | ICO | C | CCO | SC |
|---|---|---|---|---|---|---|---|---|---|---|---|---|---|---|---|---|---|---|---|---|---|---|---|---|
| I | 1 | - | - | - | - | - | - | - | - | - | - | - | - | - | - | - | - | - | - | - | - | - | - | - |
|  | 2 | - | - | - | - | - | - | - | - | - | - | - | - | - | - | - | - | - | - | - | - | - | - | - |
|  | 3 | - | - | - | - | - | - | - | - | - | - | - | - | - | - | - | - | - | - | 3 | - | - | - | - |
|  | 4 | - | - | - | - | - | - | - | - | - | - | - | - | - | - | - | - | - | - | - | - | - | - | - |
|  | 5 | - | - | - | - | - | - | - | - | - | - | - | - | - | - | - | - | - | - | - | - | - | - | - |
|  | 6 | - | - | - | - | - | - | - | - | - | - | - | - | - | - | - | - | - | - | - | - | - | - | - |
|  | 7 | - | - | - | - | - | - | - | - | - | - | - | - | - | - | - | - | - | - | - | - | - | - | - |
|  | 8 | - | - | - | - | - | - | - | - | - | - | - | - | - | - | - | - | - | - | - | - | - | - | - |
| II | 9 | - | - | - | - | - | - | - | - | - | - | - | - | - | - | - | - | - | - | - | - | - | - | - |
|  | 10 | - | - | - | 1 | - | - | - | - | - | - | - | - | - | - | - | - | - | - | - | - | - | - | - |
|  | 11 | - | - | - | - | 3 | - | - | - | - | - | - | - | - | - | - | - | - | - | - | - | - | - | - |
|  | 12 | - | - | 115 | - | - | - | 1 | - | - | - | - | - | - | - | - | 118 | - | - | 2 | - | - | - | - |
|  | 13 | - | - | - | - | - | - | 2 | - | - | - | - | 1 | - | - | - | - | - | - | - | - | - | - | - |
|  | 14 | - | - | - | - | - | - | - | - | - | - | - | - | - | - | - | - | - | - | - | - | - | - | - |
|  | 15 | - | - | - | - | - | - | - | - | - | - | - | - | - | - | - | - | - | - | - | - | - | - | - |
|  | 16 | - | - | - | - | - | - | - | - | - | - | - | - | - | - | - | - | - | - | - | - | - | - | - |
| III | 17 | - | - | - | - | 128 | - | >300 | - | - | - | >300 | >300 | - | >300 | - | >300 | >30 0 | >30 0 | >30 0 | >300 | - | - | - |
|  | 18 | - | - | 1 | >300 | >300 | - | >300 | - | - | - | >300 | >300 | - | >300 | >300 | >300 | 5 | 68 | - | - | - | - | - |
|  | 19 | - | - | - | - | - | - | 246 | - | - | - | - | >300 | - | - | - | - | >30 0 | - | - | - | - | - | - |
|  | 20 | - | - | 172 | 37 | - | - | 10 | - | - | - | >300 | - | - | - | >300 | >300 | - | - | 207 | - | - | - | - |
|  | 21 | - | - | 162 | 193 | - | - | - | - | - | - | - | - | - | - | - | >300 | - | - | - | 159 | - | - | - |
|  | 22 | - | - | 76 | - | - | - | >300 | - | - | - | >300 | >300 | - | >300 | >300 | >300 | - | - | - | - | - | - | - |
|  | 23 | - | - | >300 | >300 | - | - | >300 | - | - | - | >300 | >300 | >300 | >300 | - | - | - | - | - | >300 | 73 | - | - |
|  | 24 | - | - | - | - | - | - | - | - | - | - | - | - | >300 | >300 | - | - | - | - | - | - | 60 | - | - |
|  | 25 | - | - | 11 | 163 | 3 | - | 20 | - | - | - | 51 | >300 | - | 48 | 18 | >300 | >30 0 | 261 | - | - | - | - | - |

S : Spleen, T : Tonsil, ML : Mesenteric lymphnode, MRL : Mandibular lymphnode, ICL : Ileocecal lymphnode, HL : Hepatic lymphnode, Da : Duodenum ascending, Dd : Duodenum descending, J1, J2, J3 : Jejunum, IP1, IP2 : Ileum proximal, IM1, IM2 : Ileum mid, ID1, ID2 : Ileum distal, ICO : Ileocecal orifice, C : cecum, CCO : Cecocolic orifice, SC : Spiral colon

COMPOSITIONS FOR ELICITING AN IMMUNE RESPONSE AGAINST *MYCOBACTERIUM AVIUM* SUBSPECIES *PARATUBERCULOSIS*

CROSS-REFERENCE TO RELATED APPLICATIONS

This application claims priority to and the benefit of co-pending U.S. provisional patent application Ser. No. 61/094,552 (filed Sep. 5, 2008) and Ser. No. 60/979,822 (filed Oct. 13, 2007), both of which are incorporated herein by reference in their entireties.

STATEMENT REGARDING FEDERALLY SPONSORED RESEARCH OR DEVELOPMENT

Not applicable

REFERENCE TO APPENDIX

Not applicable

FIELD OF THE INVENTION

The present invention relates generally to stimulation of immunological responses, and more specifically to compositions and methods for stimulating prophylactic or and therapeutic immunological responses against *Mycobacterium avium* subspecies *paratuberculosis.*

BACKGROUND OF THE INVENTION

*Mycobacterium avium* subspecies *paratuberculosis* (MAP) is the causative agent of Johne's disease (JD), which causes chronic granulomatous enteritis in ruminants. Clinically affected animals develop chronic diarrhea and progressive weight loss that eventually results in death, while subclinically infected animals mainly have decreased production of milk. JD is of tremendous economic importance to the worldwide dairy industry, causing major losses due to reduced production and early culling of animals with estimates of 20% of U.S. dairy herds affected and costs of $220 million per year to the dairy industry (Wells, et al. 2000. J. Am. Vet. Med. Assoc. 216: 1450-1457). Cattle are most susceptible to infection with this organism within the first 6 months of life, but disease typically does not become evident until 3 to 5 years of age. Infection occurs by ingestion of contaminated manure, colostrum, or milk from infected cows (Sweeney, 1996. Vet. Clin. N. Am. Food Anim. Pract. 12:305-312). Fetal infection also occurs, particularly in pregnant cows with advanced disease (Sweeney, et al. 1992. Am. J. Vet. Res. 53:477-480). Moreover, the significance of MAP has increased significantly because of its potential role as a causative agent of Crohn's disease in people (Chamberlin, et al. Aliment Pharmacol Ther 2001; 15(3):337-46; Naser S A, et al. Mol Cell Probes 2002; 16(1):41-8).

The currently approved JD vaccine for field use is an oil suspension of a killed strain of MAP, which has significant limitations. Primarily, the efficacy of this vaccine is questionable with varying results in different vaccination trials Another concern is the interference of whole cell bacterins with diagnostic testing, since vaccinated animals have false positive reactions for tuberculosis and *paratuberculosis*). Thus, the demand for improved vaccines is on the rise, but they need to be potent and at the same time should not interfere with the diagnosis of tuberculosis and JD. To achieve this goal, several approaches have been tried, which include recombinant vaccines, DNA vaccines and subunit vaccines 13; Shin S J, et al. Infect Immun 2005; 73(8):5074-85). However, there continues to be a need for the development for improved MAP vaccines.

SUMMARY OF THE INVENTION

The present invention provides compositions and methods for stimulating an immunological response in mammals against MAP. The compositions comprise a novel 79 kDa recombinant polypeptide referred to herein as "Map74F". Map74F was generated by linking a ~17.6-kDa C-terminal fragment of Map3527 protein to a fragment of Map1519 protein, followed at the C terminus by a 14.6-kDa N-terminal portion of Map3527 protein.

Figure 2A:
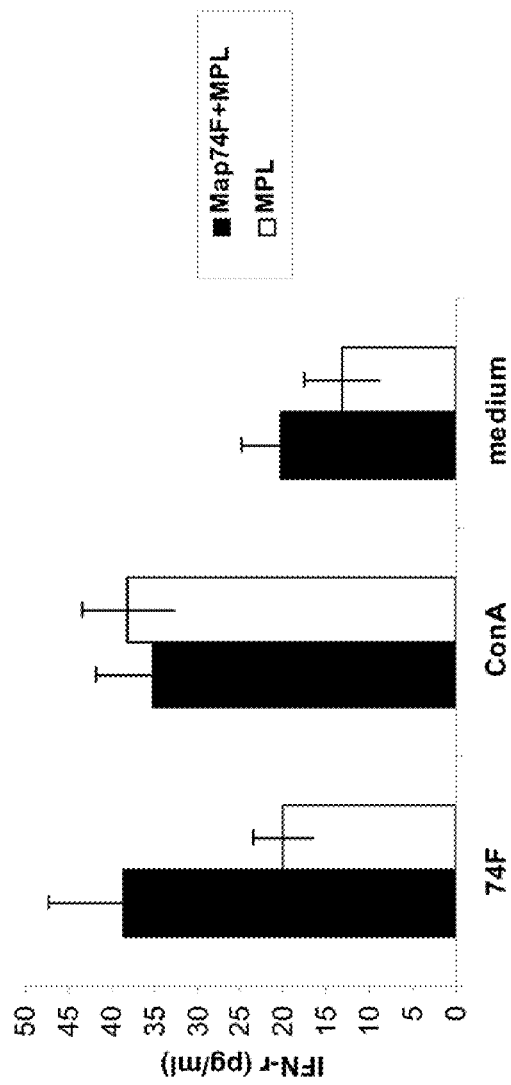
Figure 2B:
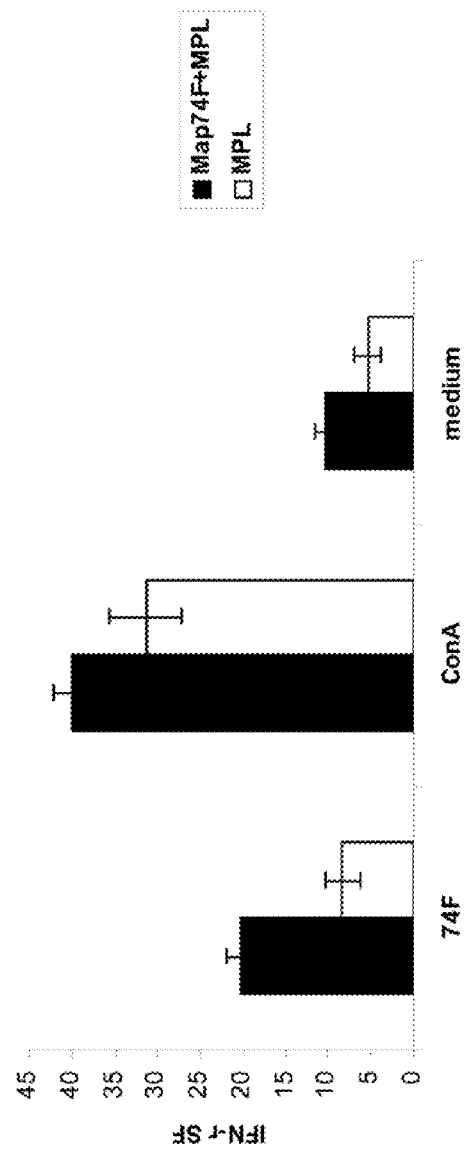
Figures 2C, 2D:
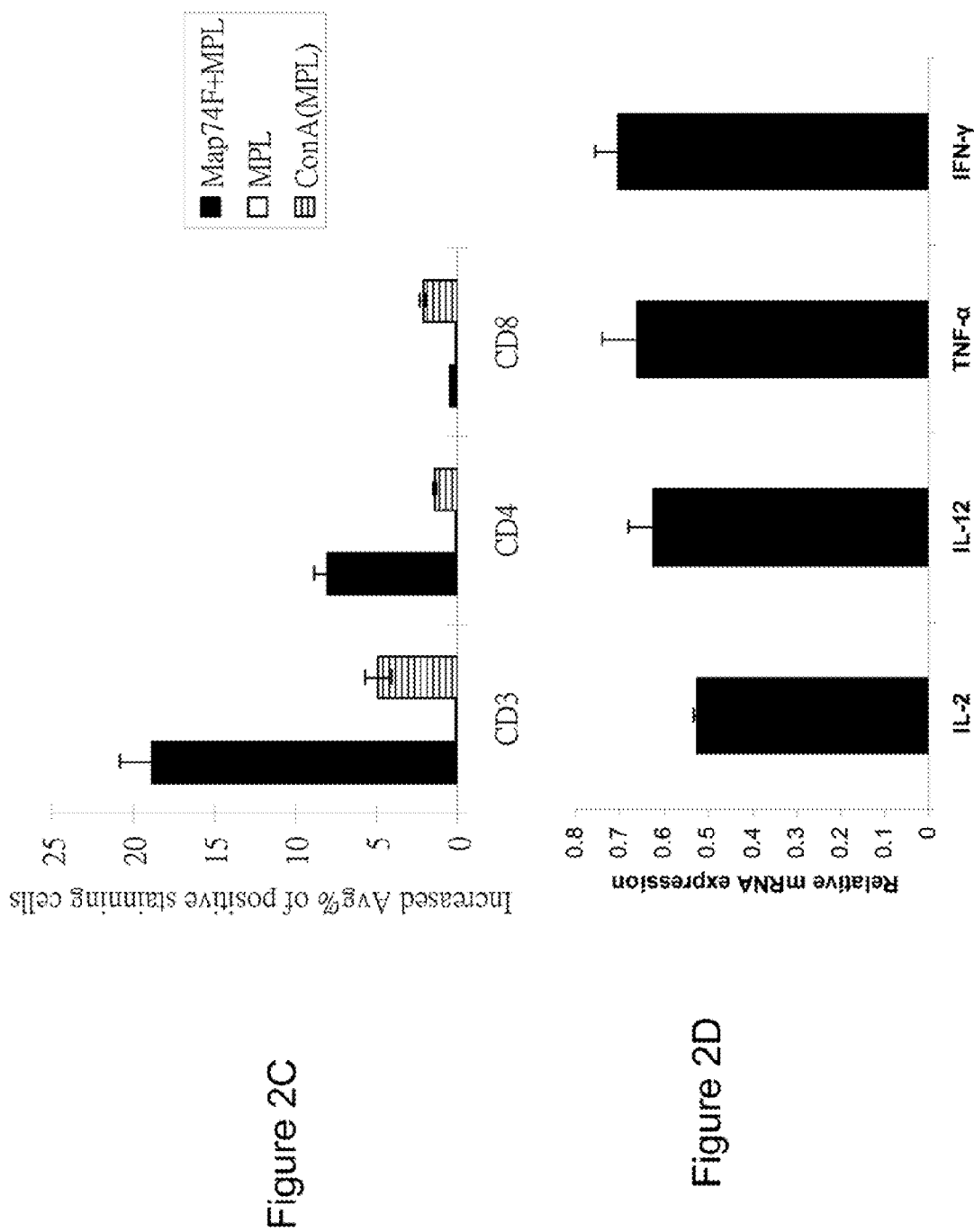

In addition to Map74F, the compositions of the invention may also comprise other MAP proteins, such as MAP proteins 85A, 85B, 85C, 35kDa, SOD, MptC, MptD and ESAT-6 like protein, and combinations thereof.

The method comprises administering the composition to a mammal in an amount effective to stimulate an immunological response against MAP bacteria. The method is expected to be of benefit to any mammal susceptible to MAP infection, but is particularly beneficial for ruminants.

The compositions can be formulated with standard pharmaceutical carriers and can be administered via any of a variety of conventional routes. The compositions can be administered at any time to an animal susceptible to contracting MAP infection or to an animal that is infected with MAP. However, it is preferable to administer the compositions prior to MAP infection, such as by administration to pregnant animals that can transfer prophylactic immunologic components to their newborns via colostrum, or by administration during the period from one to five weeks after birth.

BRIEF DESCRIPTION OF THE FIGURES

FIG. 1A provides a schematic representation of Map74F construct. Map74F was generated by sequential linkage from its N to C terminus of ORFs encoding a C-terminal fragment of Map3527 protein linked to an ORF encoding amino acids 1-460 of Map1519 protein, and terminating with an ORF encoding an N-terminal fragment of Map3527. The ORF encoding Map74F is 2397 nucleotides (nt) and it encodes a 799-aa polypeptide with a predicted molecular mass of ~79 kDa.

FIG. 1B provides a photographic representation of Coomassie Blue-stained 10% SDS-PAGE of *E. coli* lysates from *E. coli* (BL21/pLysE) transformed with an expression vector encoding Map74F. The cells were grown and induced with 1 mM IPTG. The lanes depict lysates before (lane UI) or 3 hours after (lane I) IPTG induction. Purified recombinant Map74F is shown in lane P along with molecular mass marker (lane M).

FIG. 2A-2D provide graphical representations of data obtained from mice sacrificed 3 weeks after booster vaccination. Spleen cells from mice, administered with Map74F+Monophosphoryl lipid A (MPL) and MPL alone were stimulated for 2 days with 10 μg/ml of Map74F, ConA and medium. For the data presented in FIG. 2A, culture supernatants were assayed for IFN-γ levels by ELISA. For the data presented in FIG. 2B, ELIspot assay to determine the relative numbers of IFN-γ-expressing cells in single-cell spleen suspensions of immunized and control mice stimulated with and without antigens. In FIG. 2C, data from FACS analysis of spleen cells for lymphocyte subset populations collected from the vaccinated (Map74F+MPL) and control animals (MPL, ConA-MPL) after stimulation with the recombinant and control antigens are presented. In FIG. 2D, data are presented for cytokine mRNA expression in response to Map74F normalized to the housekeeping gene GAPDH. Data are representative of three independent experiments.

Figure 3A:
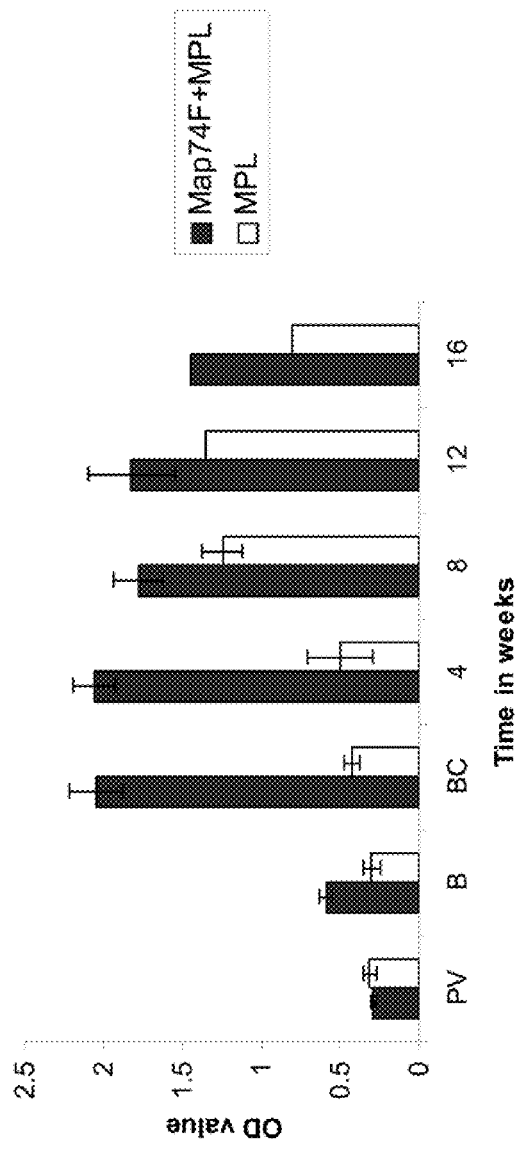
Figure 3B:
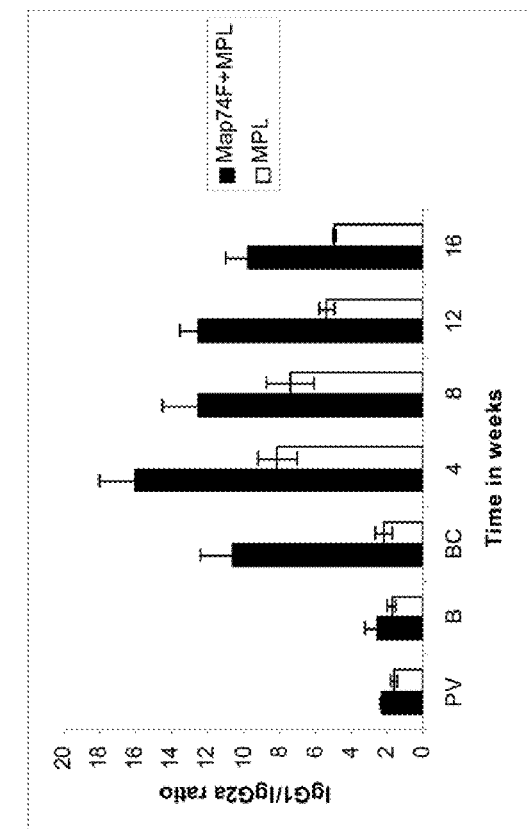

FIGS. 3A and 3B present data obtained from sera collected from vaccinated and control animals at different time points (Pre-vaccination/primary vaccination (PV), booster vaccination (B), before challenge (BC), 4, 8, 12, and 16 weeks after challenge) and checked for antibody response. The data presented in FIG. 3A are from sera tested for Map74F specific antibodies. FIG. 3B presents data testing for IgG1:IgG2 ratios by ELISA. Data are representative of three independent experiments.

Figure 4B:
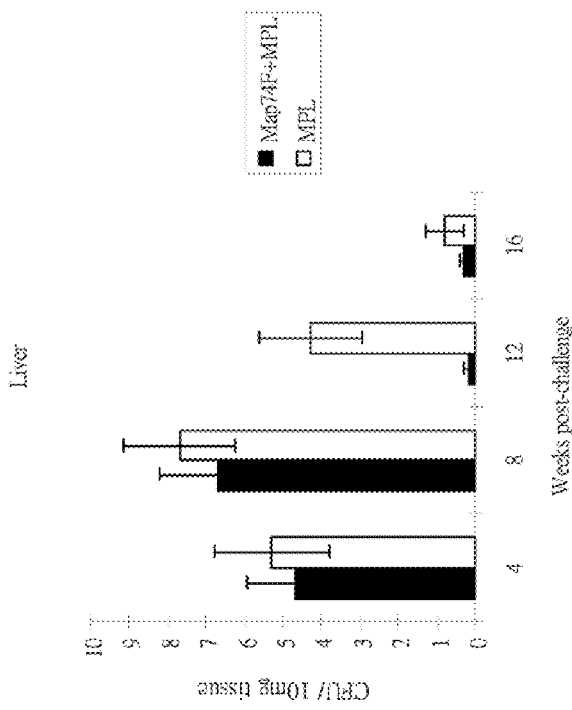
Figure 4A:
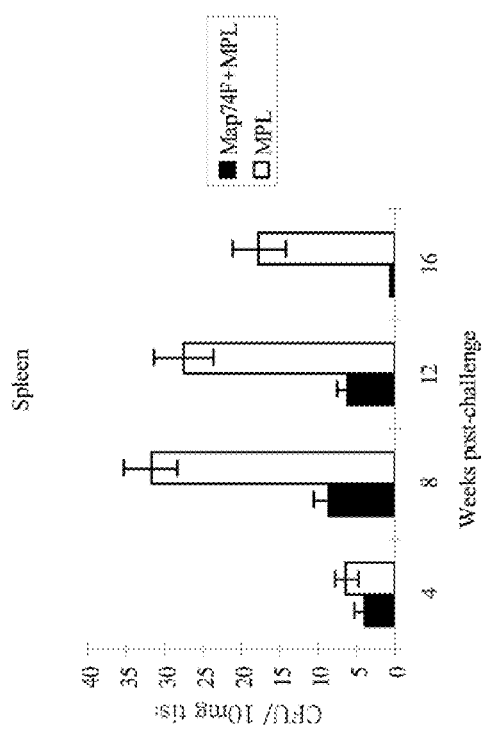

FIGS. 4A and 4B provide graphical depictions of data showing expression of protective immunity in spleen (FIG. 4A), liver (FIG. 4B) and mesenteric lymph node (MLN) (FIG. 4C) conferred by vaccination with Map74F+MPL. Map74F significantly reduced MAP burden in the spleen (at 8-16 weeks after challenge), liver (at 12-16 weeks after challenge) and MLN (at 8-16 weeks after challenge). Data are representative of three independent experiments.

Figure 5A:
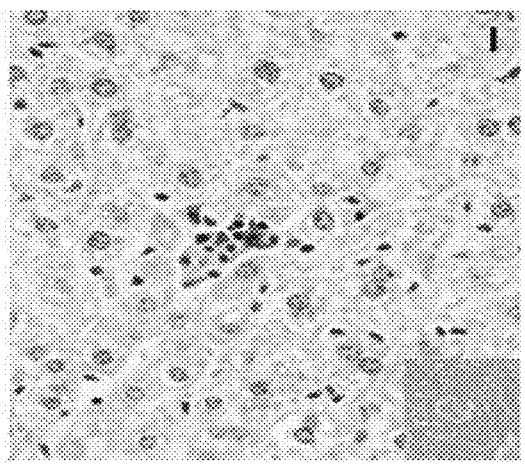
Figure 5B:
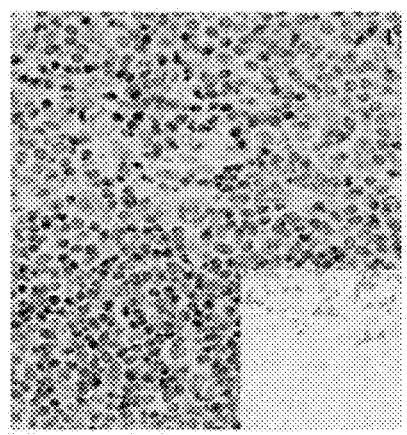
Figure 5C:
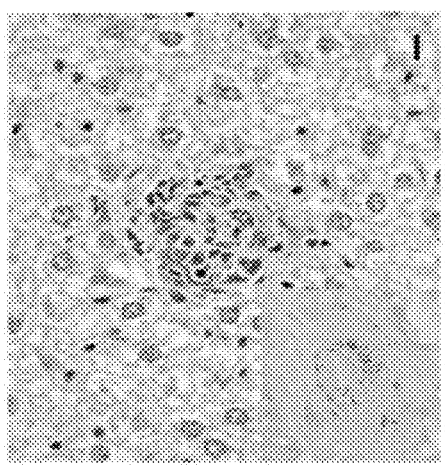
Figure 5D:
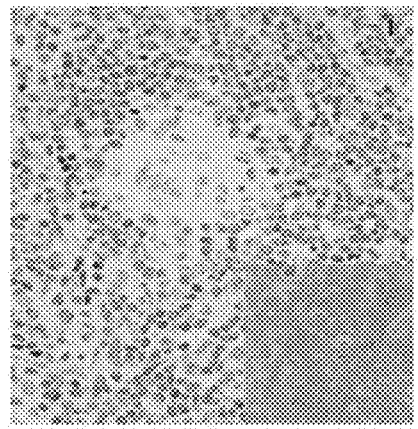

FIGS. 5A-5D provide photographic representations of histopathologic examination of vaccinated and non-vaccinated mouse tissues. FIG. 5A is representative of liver from an un-vaccinated control mouse. Numerous large granulomas are randomly dispersed throughout the liver. Hematoxylin and Eosin. Bar=100 um. Insert: Higher magnification of a granuloma demonstrating numerous acid-fast bacilli. Ziehl-Neelsen staining. FIG. 5B is representative of liver from a mouse vaccinated with Map74F. Only sparse numbers of small lymphoid aggregates accompanied by a few macrophages are present. FIG. 5C is representative of spleen from an un-vaccinated control mouse showing occasional granulomas in the white pulp. FIG. 5D is representative of spleen from a mouse vaccinated with Map74F. The white and red pulp are devoid of granulomas. Hematoxylin and Eosin staining. Bar=100 nm. Insert: Higher magnification of a granuloma demonstrating the absence of acid-fast bacilli. Ziehl-Neilsen staining.

Figure 6A:
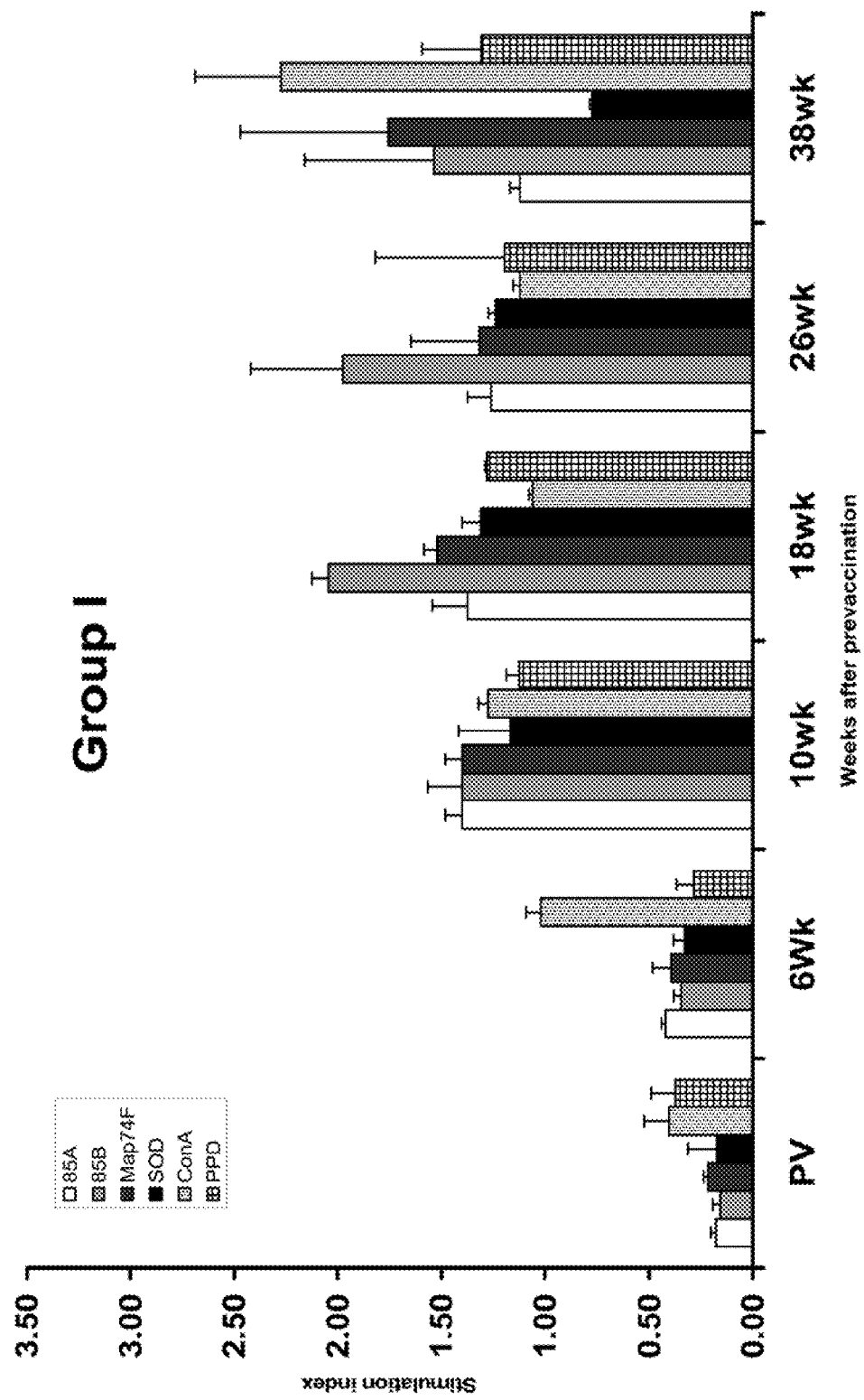
Figure 6B:
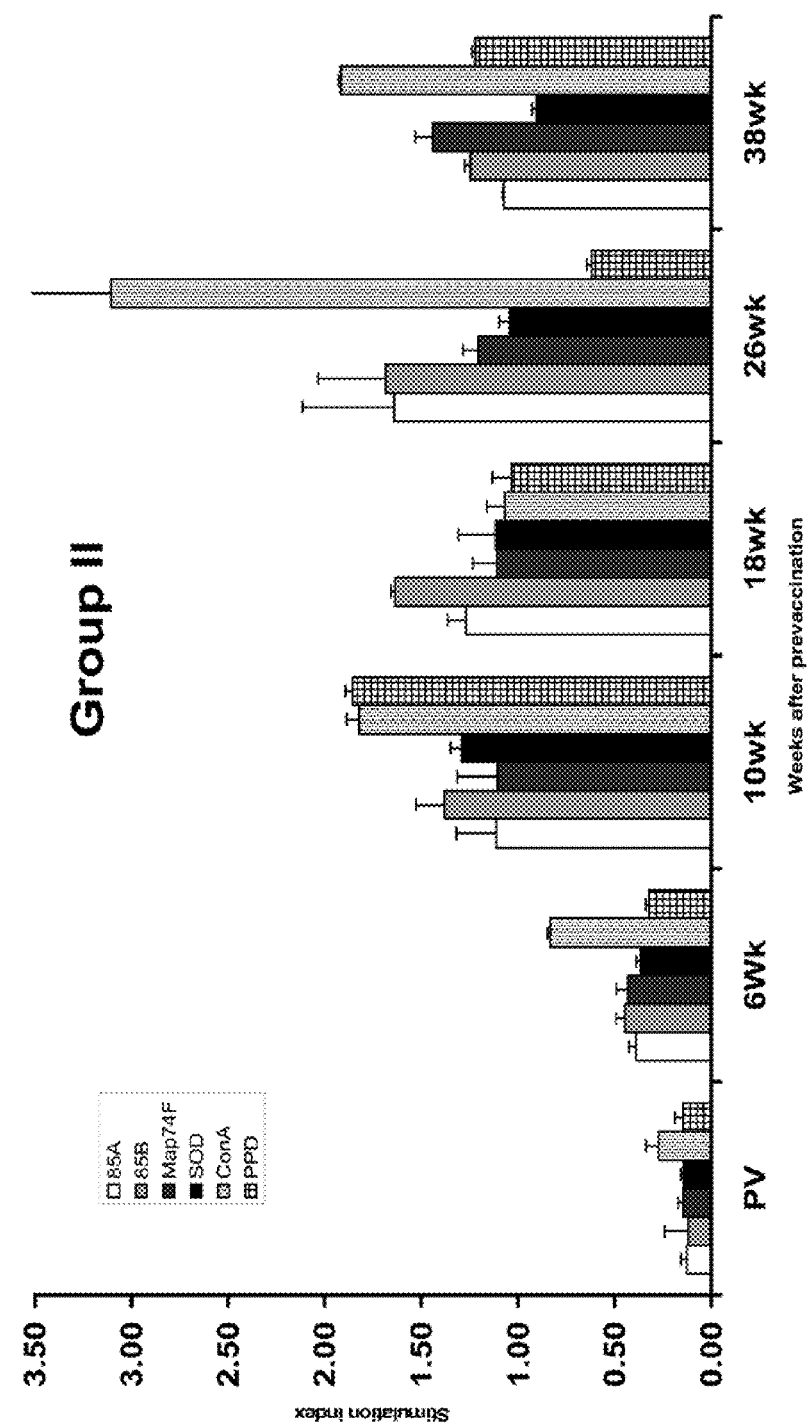
Figure 6C:
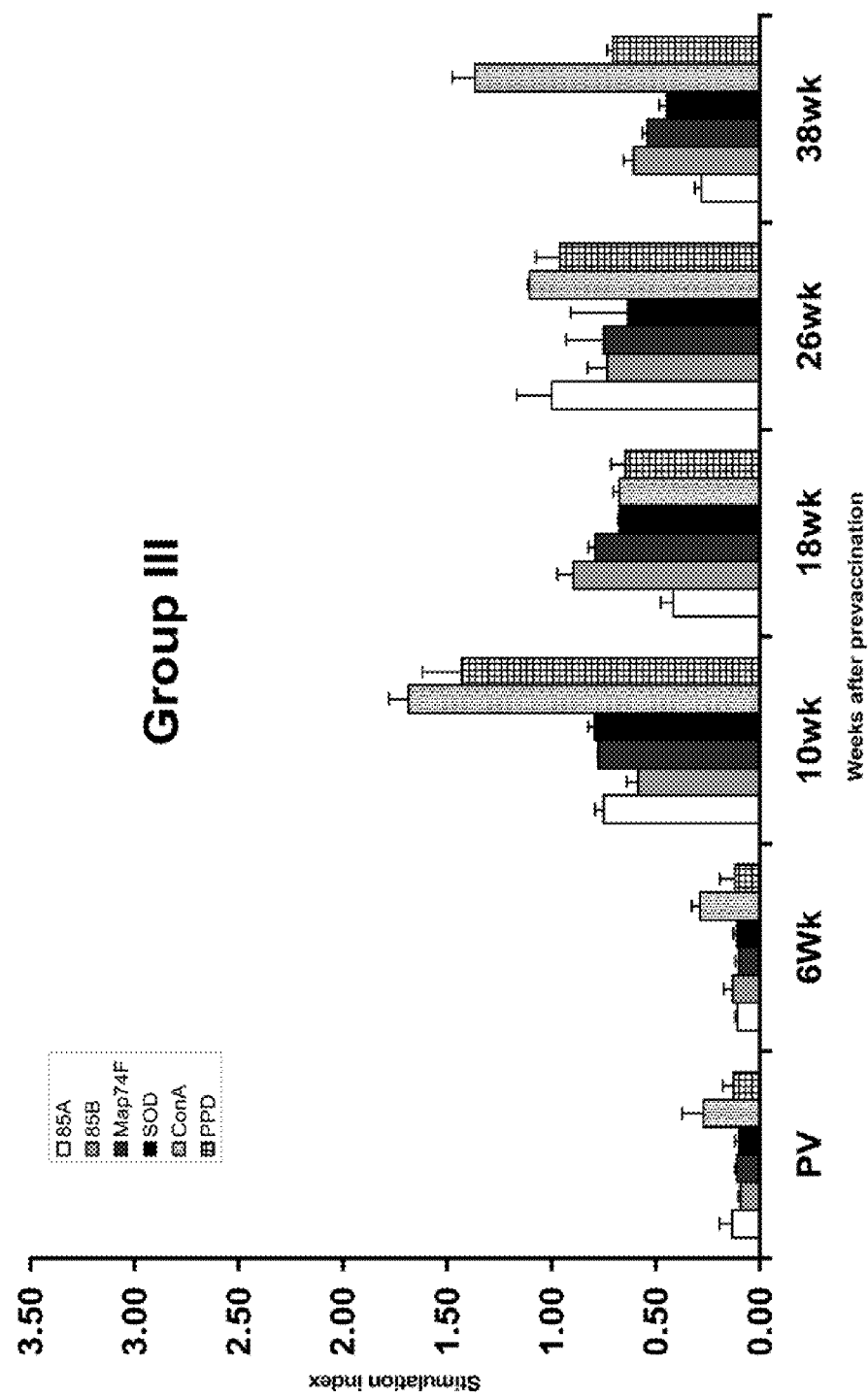

FIGS. 6A-6C provide graphical depictions of data showing lymphoproliferative responses of peripheral blood mononuclear cells (PBMC) from immunized (group I and II) and control (group III) animals to the recombinant antigens (85A, 85B, Map74F and SOD), Con A and PPD. The results are expressed as stimulation index (SI), and the error bars indicate standard deviation from the mean.

Figure 7A:
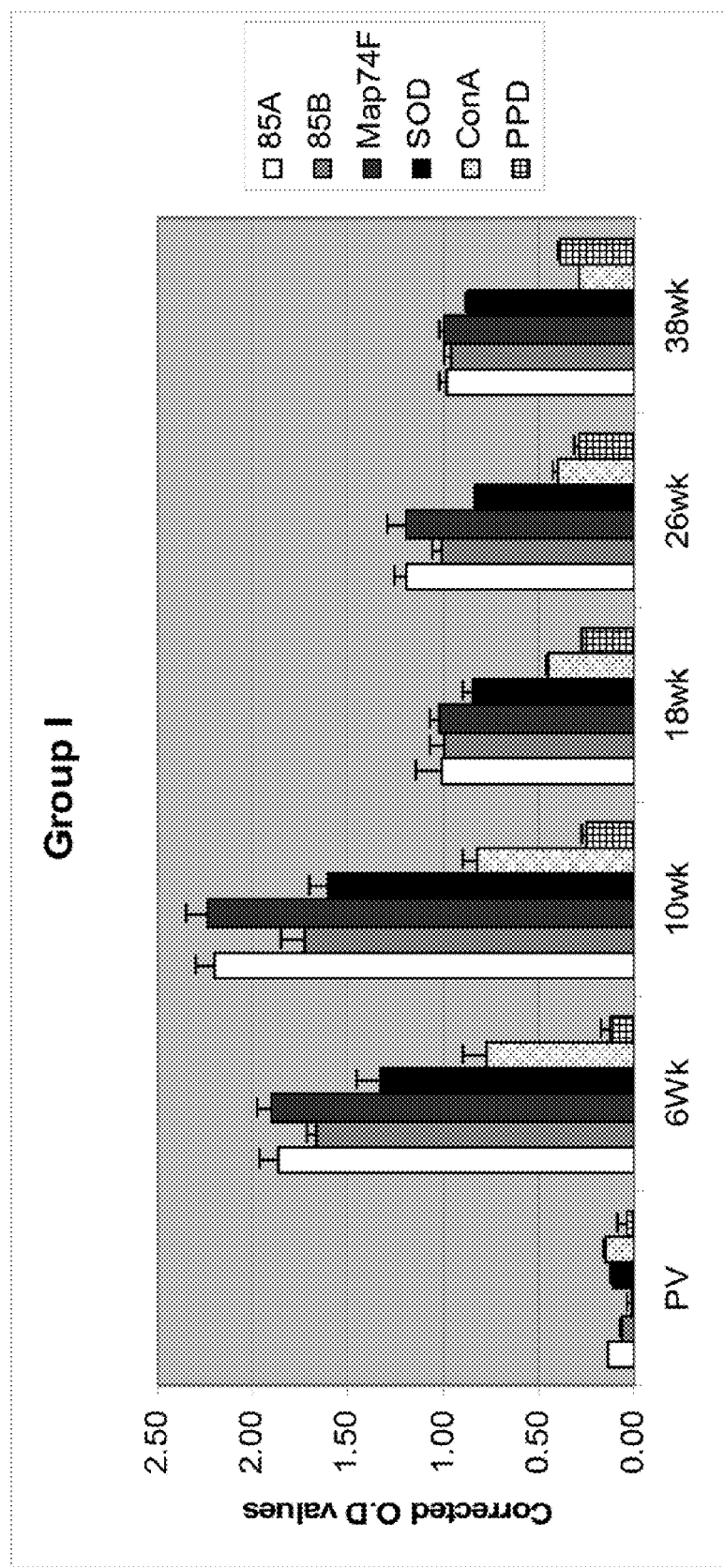
Figure 7B:
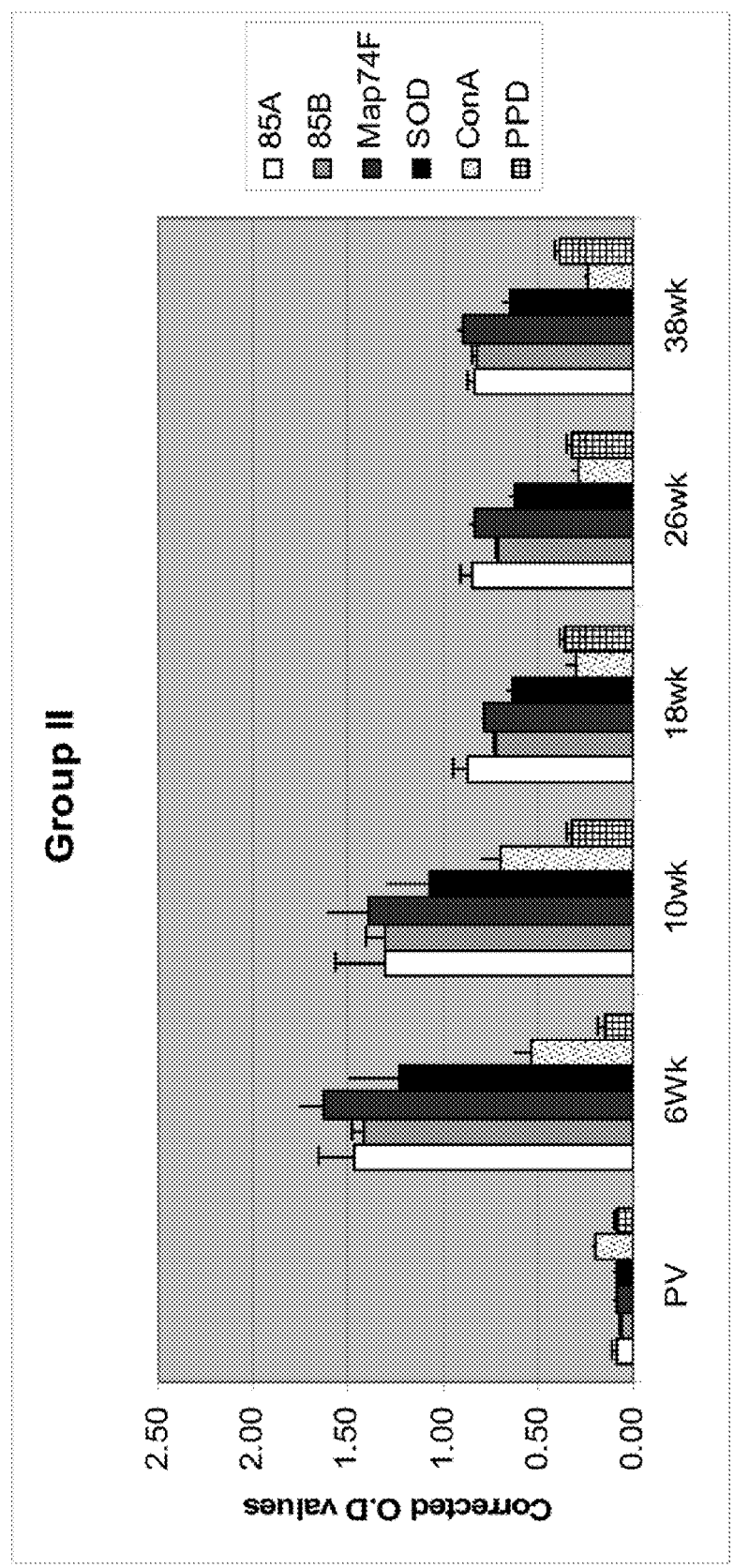
Figure 7C:
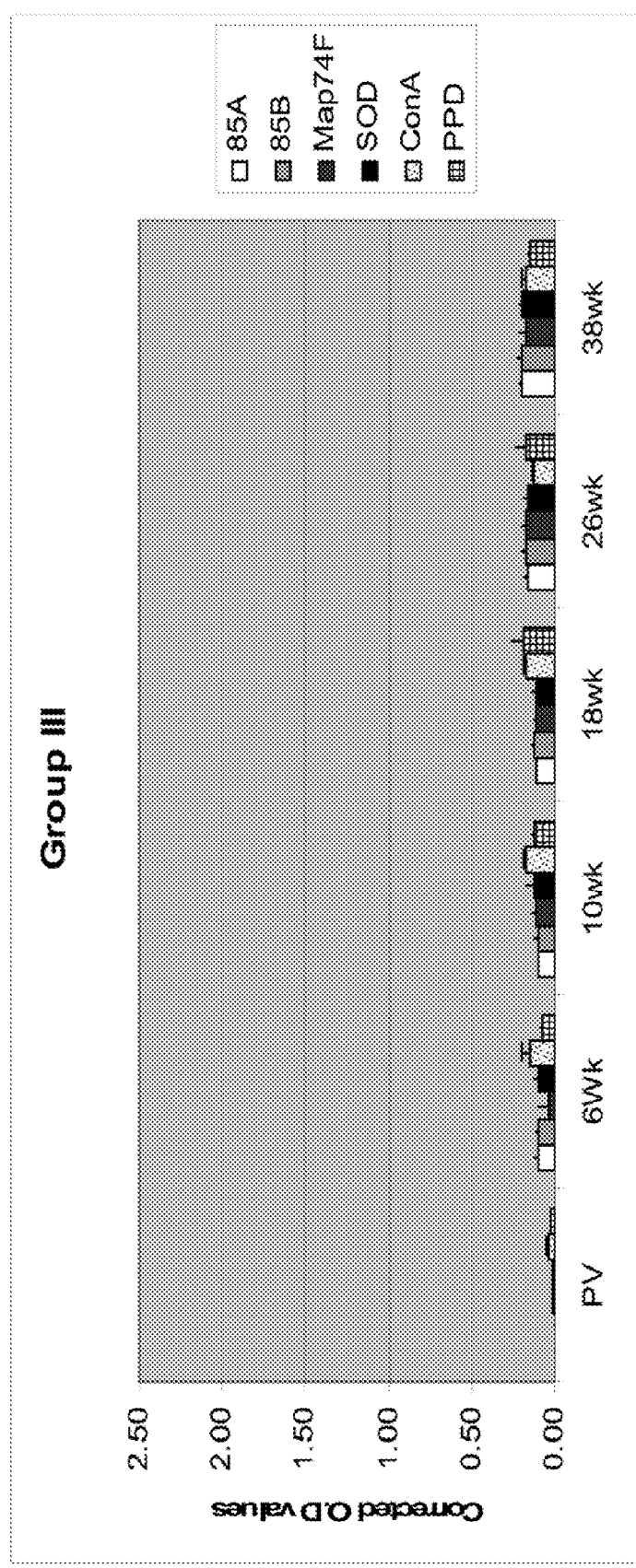

FIGS. 7A-7C provide graphical depictions of data showing antigen specific IFN-γ response of PBMC from immunized (group I and II) and control (group III) animals. Results are expressed as OD values and error bars indicate standard deviation from the mean.

FIGS. 8A-8F provide graphical depictions of data showing expression of lymphocyte subsets from PBMC collected from the immunized groups (I and II) and the control group (III) at specified times after stimulation with the recombinant and control antigens as analyzed by flow-cytometry. Results are expressed as percentage of cells with positive staining relative to the un-induced sample (cultured with medium). Error bars indicate standard deviation from the mean.

Figure 9A:
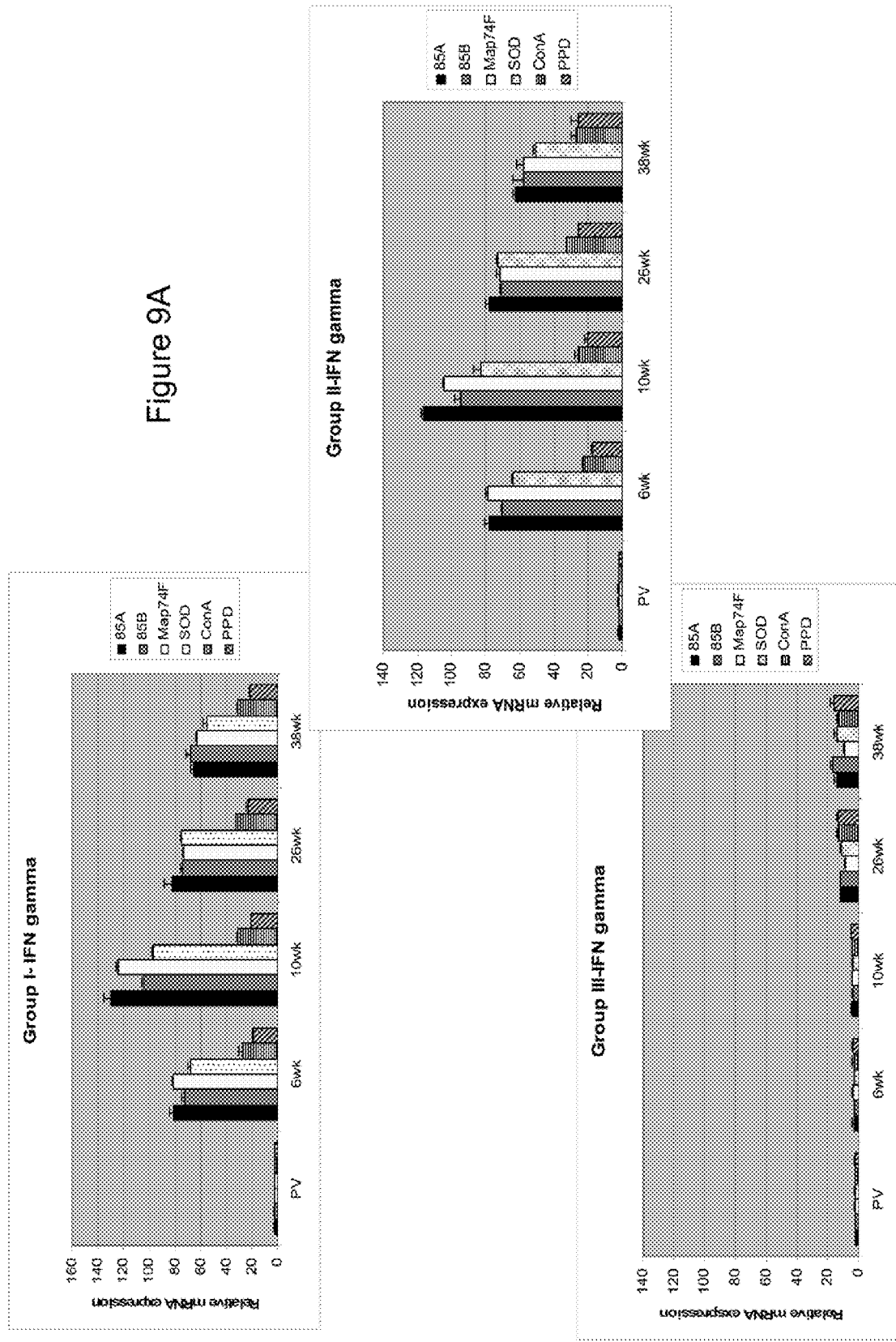

FIGS. 9A and 9B provide graphical depictions of data showing cytokine gene mRNA expression in response to recombinant antigens in the immunized groups (I and II) and control group (III). Results are expressed as the mean fold increase over un-stimulated PBMC, which served as calibrators. Error bars indicate standard deviation from the mean.

Figure 10:
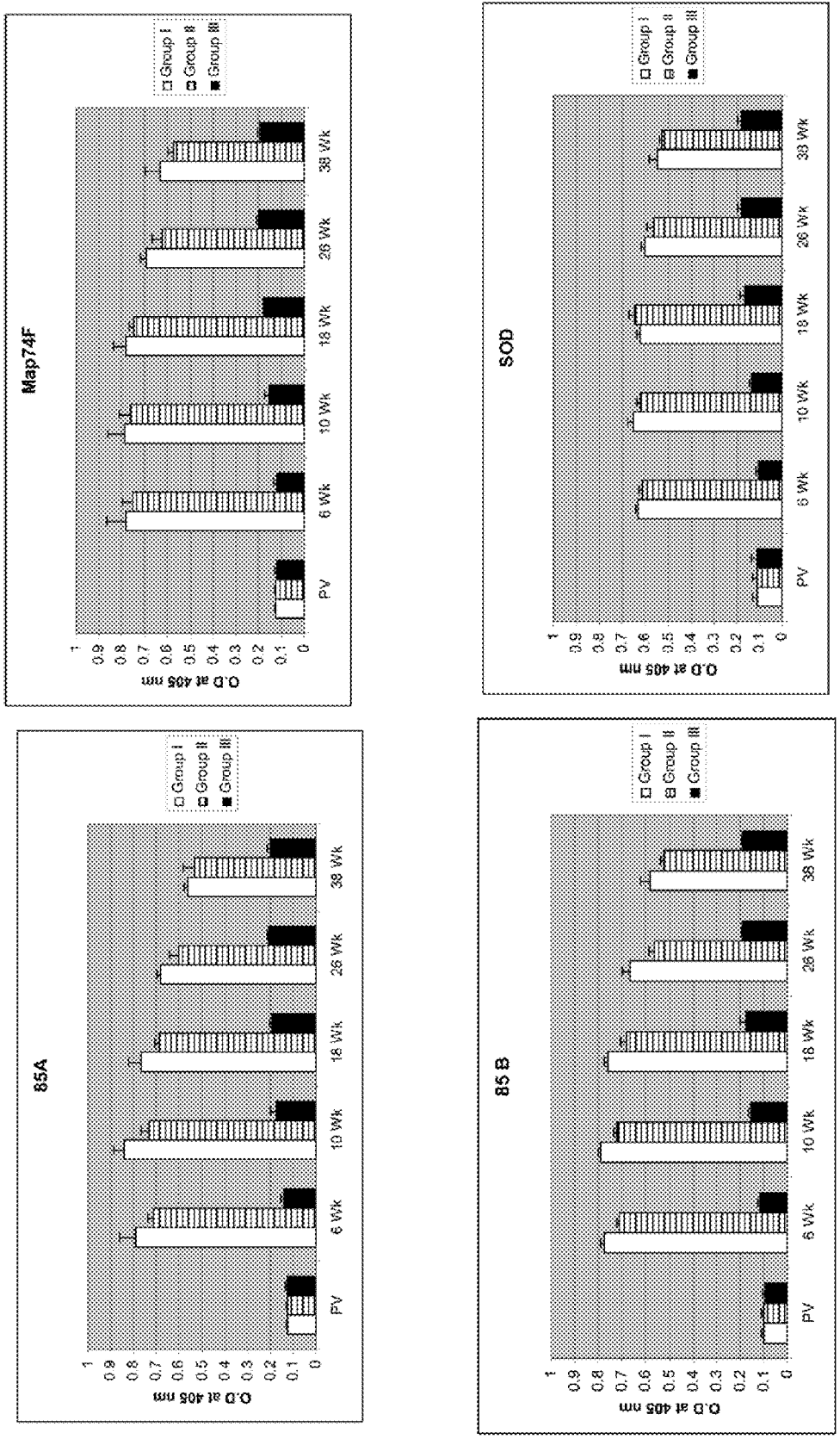

FIG. 10. Antibody responses to individual recombinant antigens in the vaccinated group I and II animals and the control group III animals. Error bars represent standard deviation from the mean.

FIG. 11 provides a tabular summary of MAP culture results (CFU) measured in various tissues collected at necropsy.

DETAILED DESCRIPTION OF THE INVENTION

The present invention provides compositions and methods for stimulating an immune response against MAP in an animal. The compositions comprise a recombinant polypeptide referred to herein as Map74F. The open reading frame (ORF) encoding Map74F is 2397 nucleotides in length and codes for a 799 amino acid polypeptide. The sequence of the Map74F protein is provided in SEQ ID NO: 1. Map74F has a molecular mass calculated based upon its amino acid composition to be 79 kDa, despite its apparent molecular mass of about 74 kDa as estimated by SDS-PAGE analysis. The sequence provided in SEQ ID NO:1 is shown without an optional purification tag, such as a histidine tag.

Map74F was constructed by linking from N-terminus to C-terminus a ~17.6-kDa C-terminal fragment of Map3527 protein, a 46.8 kDa fragment of Map 1519 protein, followed by a ~14.6-kDa N-terminal fragment of Map3527 protein. A schematic representation of Map74F is provided in FIG. 1.

The complete amino acid sequences of Map3527 and Map1519 are provided as SEQ ID NO:2 and SEQ ID NO:3, respectively. The 17.6-kDa C-terminal fragment of Map3527 protein present in Map74F is represented by amino acids 183-361 of SEQ ID NO:2. The 46.8 kDa fragment of the Map1519 protein present in Map74F is represented by amino acids 1-460 of SEQ ID NO:3. The 14.6-kDa N-terminal fragment of Map3527 present in Map74F is represented by amino acids 33-180 of SEQ ID NO:2. It is expected that longer fragments of Map1519 and of the N- and C-termini of Map3527 could be included in a recombinant protein that would be useful in the method of the invention.

In addition to MAP74F, the compositions of the invention may comprise other agents that can stimulate an immune response against MAP bacteria. For instance, the compositions may comprise one or more other MAP proteins, such as MAP proteins 85A, 85B, 85C, 35 kDa, Superoxide dismutase (SOD), MptC, MptD and ESAT-6 like protein, and combinations thereof. These proteins are described in U.S. application Ser. No. 11/816,365, and the description of these proteins, DNA sequences encoding them, and methods of using the proteins and the DNA encoding them in compositions for stimulating an immunological response against MAP are incorporated herein by reference.

In one embodiment, the composition comprises MAP74F and one or more of the MAP proteins 85A, 85B or SOD. The DNA sequence encoding the MAP 85A gene and the amino acid sequence of the 85A gene are provided in GenBank accession no. AF280067 (Oct. 10, 2003, entry). The DNA sequence encoding the MAP 85B gene and the amino acid sequence of the 85A gene is provided in GenBank accession no. AF219121 85B gene (Nov. 21, 2002 entry). The DNA sequence encoding the MAP 85C gene and the amino acid sequence of the 85C gene is provided in GenBank accession no. AF280068 (Nov. 21, 2002 entry). The DNA sequence encoding the MAP SOD gene and the amino acid sequence of the SOD gene is provided in GenBank accession no. AF 180816 (Nov. 30, 2001 entry).

The method of the invention comprises administering a composition comprising Map74F to a mammal in an amount effective to stimulate an immune response against MAP. The stimulated immune response may comprise stimulation of any component of the immune system, including but not limited to generation of antibodies reactive to MAP antigens, stimulation of lymphocyte proliferation, production of Th1-associated cytokines, such as IFN-γ, and combinations of the foregoing.

Map74F may be administered to an animal in the form of a vector. For example, nucleic acid sequences encoding Map74F may be cloned into the genome of a bacterium (e.g., *Salmonella*) or a virus (e.g., bovine herpesvirus-1 (BHV-1)), and the resulting recombinant bacterium or virus may be administered to animals. Thus, the present invention also includes bacterial and viral vectors expressing Map74F. Also contemplated within the scope of this invention are DNA vaccine methodologies wherein nucleic acid molecules encoding Map74F, either alone or in combination with an adjuvant or transfection-facilitating agent, are administered directly to animals.

The method can provide benefit to any animal susceptible to MAP infection. The compositions and method are particularly well suited for prophylaxis or therapy for MAP infection of ruminants, including but not limited to cattle, sheep, goats, deer and elk, antelope, and buffalo. In one embodiment, the method can be used for prophylaxis or therapy of Johne's Disease.

The compositions can be administered to any MAP infected or non-infected animal. Administration of the compositions to infected animals according to the method of the invention is considered to stimulate a therapeutic immunological response. However, the invention also includes administering the compositions prior to MAP infection to stimulate a prophylactic response. For example, the compositions can be administration to a pregnant animal that can transfer prophylactic immunologic components to their non-infected newborns via colostrum or milk during lactation. Alternatively, the compositions can be administered during the period from one to five weeks after birth to provide a prophylactic effect which can prevent MAP infection or reduce the severity of disease if infection occurs. Thus, in one embodiment, the method of the invention is prophylactic for MAP infection, while in another embodiment, the method is therapeutic for MAP infection.

The compositions can be formulated with standard pharmaceutical carriers and can be administered via any of a variety of conventional routes. Some examples of acceptable pharmaceutical carriers for use with proteins are described in Remington's Pharmaceutical Sciences (18th Edition, A. R. Gennaro et al. Eds., Mack Publishing Co., Easton, Pa., 1990).

The compositions used in the method of the invention may also comprise adjuvants. Any conventional adjuvant can be used.

In one embodiment, the adjuvant may be Monophosphoryl lipid A (MPL), which may be provided in combination with synthetic trehalose dicorynomycolate. In another embodiment, the adjuvant may be dimethydioctadecyl ammonium bromide (DDA).

The compositions of the invention can be administered by any acceptable route. Suitable routes of administration include oral, mucosal and parenteral (e.g., intravascular, intramuscular, and subcutaneous injection). The compositions can be administered at any time to an animal susceptible to contracting MAP infection or to an animal that is infected with MAP.

Those skilled in the art will recognize that the amount of MAP74F and any other antigenic agents in the composition administered to a particular animal will depend on a number of factors, such as the route of administration, and the size, physical condition and the MAP status of the animal, and can be adjusted by those skilled in the art to achieve a desired result. The compositions can be used in a single administration or in a series of administrations to boost the immunological response. In general, a total dosage of between 10-200 μg of protein can be administered.

The following examples describe the various embodiments of this invention. These examples are illustrative and are not intended to be restrictive.

Example 1

This Example provides a description of the cloning, expression and purification of Map74F.

Generation of a Tandem Linked ORF Encoding Map74F

Map74F was generated by the sequential linkage in tandem of the ORFs of the ~17.6-kDa C-terminal fragment of Map3527 to an ORF encoding a Map1159 protein having a molecular mass of 46.8 kDa, followed at the C terminus with ~14.6-kDa N-terminal portion of Map3527.

Generation of Map3527c Construct Devoid of a Stop Codon.

The 5' and 3' oligonucleotides to the C-terminal portion of Map3527 (Map3527c) were designed as follows: 5' (TA CATATG CAT CAT CAT CAT CAT CAT CTC AAC CAG AGC GTC TCG GC 3' (SEQ ID NO:4)) and (5' TA GAATTC GGC CGG CGG CCC CTC CGC C 3' (SEQ ID NO:5)). The 5' oligonucleotide contained an NdeI restriction site preceding an ATG initiation codon, followed by nucleotide sequences encoding six histidine residues (italics). The 3' oligonucleotide contained an EcoRI restriction site. These oligos were used to amplify Map3527c, the carboxyl 540-nt portion (a 14.6 kDa, 180 aa residues) of Map3527 and the resulting PCR-amplified product was ligated to a PCR2.1 Topo vector. The plasmid DNA with the correct insert was digested with NdeI and EcoRI, and ligated into the pET17b expression vector cut with the same enzymes. The ligated products were transformed into *Escherichia coli* DH5α cells and one transformant with the correct insert (Map3527c) was identified by restriction enzyme digestion and DNA sequencing.

PCR Amplification of the Full-Length Coding Sequences of Map1519 and Ligation into the Map3527c-pET Plasmid.

The 5' and 3' oligos of Map1519 contained the following sequences: 5'(5'-CTA ATC GAATTC ATG TTC TAT GGG GCC TTT C-3' SEQ ID NO:6)) and 3'(5'-TA ATC GATATC CAG GAC CTT GGA CTT GTC-3' SEQ ID NO:7)). The 5' oligonucleotide contained an EcoRI restriction site. The 3' oligonucleotide had an EcoRV restriction site, followed immediately by sequences comprising the six C-terminal amino acid residues and devoid of a stop codon. The amplification of the coding sequence of Map1519 (1380 bp; a 460-aa stretch with a predicted size of ~46.8 kDa), and resulting PCR-amplified product was ligated to PCR2.1 Topo vector cut with the same enzymes. The clone with the correct insert was digested with EcoRI and EcoRV and ligated to EcoRI/EcoRV predigested Map3527c-pET plasmid. The ligated products were then transformed into *E. coli* DH5α cells, and a transformant with the correct insert (Map3527c-Map1519) was identified by restriction enzyme digestion and verified by DNA sequencing.

Cloning of the N-Terminal Fragment of Map3527 into the Map3527C-Map1519 Construct.

The 5' and 3' oligonucleotides of the N-terminal fragment of Map3527 were designed as described below: 5'(5'-AT GATATC GGG CTG GCG CCG GCG TCC-3' SEQ ID NO:8)) and 3'(5'-AT CTCGAG TCA CGC GAC CTT GCC GGC-3' SEQ ID NO:9)). The 5' oligonucleotide contained an EcoRV restriction site. The 3' oligonucleotide contained an XhoI restriction site. They were designed to amplify the N-terminal 447-bp (149-amino acid residues) portion of Map3527. The resulting PCR-amplified product was digested with EcoRV and XhoI, and ligated into the Map3527c-Map 1519 fusion pET plasmid digested with EcoRV and XhoI. The ligation mixture was used to transform $E.$ $coli$ DH5α cells and the positive clones were identified by restriction digestion and verified by DNA sequencing. The final construct, encodes a 74-kDa polyprotein (Map74F), comprising a single ORF organized in the linear order, Map3527C-Map1519-Map3527N.

Expression and Purification of Map74F Recombinant Protein

The plasmid DNA construct was transformed into $E.$ $coli$ BL21 (DE3 pLysE) cells. The transformed $E.$ $coli$ cells were plated onto LB agar supplemented with ampicillin (100 μg/mL). A single colony was inoculated into 10 mL of LB broth with ampicillin (100 μg/mL), and cultured at 37° C. overnight with shaking. The culture was diluted 1:100 in the LB broth containing ampicillin (100 μg/mL) and chloramphenicol (34 μg/m) and grown at 37° C. with shaking. After 3 hr induction with 1 mM IPTG (Invitrogen Co, Carlsbad, Calif.), cells were harvested by centrifugation (5000×g) and washed once in PBS. Cells were suspended in buffer A (50 mM TrisHCl, 1 mM EDTA, 50 mM NaCl, pH8.0) and lysed in a French cell press or cell disruptor. After spinning down the inclusion bodies, the pellets were washed three times with inclusion body washing buffer (Buffer A+1% Triton X-100) and twice with CHAPS (Sigma-Aldrich, St. Louis, Mo.) buffer (1% CHAPS in 10 mM Tris-HCl, pH8.0) in order to remove lipopolysaccharide (LPS). The inclusion bodies were dissolved in Buffer B (100 mM sodium phosphate, 10 mM Tris-HCl, 8 M urea, 2 mM PMSF (Sigma) and 20 μg/ml of leupeptin (Sigma), pH8.0) and purified with Ni-NTA agarose column (Invitrogen). Eluted fractions were checked by SDS-PAGE and the fractions containing the recombinant protein were pooled and dialyzed against 10 mM Tris-HCl (pH7.8) overnight at 4° C. for two times. The protein was passed through the Detoxi-Gel™ Endotoxin Removing Gel (Pierce, Rockford, Ill.) and the purified protein was checked for endotoxin levels by the $Limulus$ amoebocyte assay. The purified protein had negligible levels (10 pg/ml) of endotoxin.

Figure 1B:
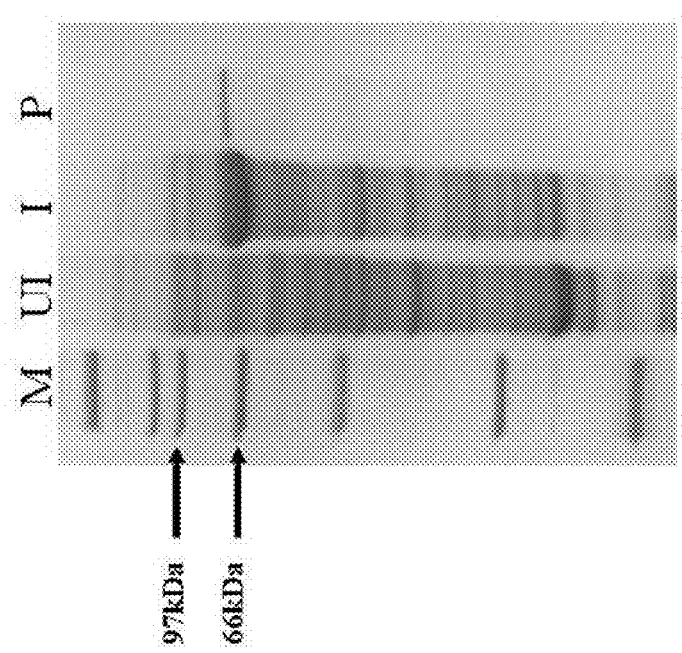

A diagrammatic representation of Map74F showing the organization and restriction enzyme sites used to construct the polyprotein is shown in FIG. 1. The ORF of Map 74F is 2397 nt long, coding for a 799 amino acid polypeptide (FIG. 1B) with a predicted molecular mass of ~79 kDa. Design and construction of the ORF resulted in the introduction of two hinge sequences (EcoRI and EcoRV) of six nucleotides, coding for two amino acids at each of the junction sites connecting the three. In addition, the ORF was designed to have six histidine residues in the N-terminus for purification using Ni-NTA matrix. After expression in $E.$ $coli$, the recombinant protein was purified from inclusion bodies and analyzed by SDS-PAGE (FIG. 1B) with yields ranging around 1.5-2.0 mg of purified protein from one liter of induced culture.

Example 2

This Example demonstrates the use of Map74F to simulate an immune response against MAP in a mouse model.

Mice have been found to be a suitable model for MAP infection studies. Bacterial load and pathology of specific organs are good indicators of the infectious status of mice following challenge with MAP. In mice, liver, spleen and mesenteric lymph nodes are the organs of choice for assessing the bacterial burden following MAP challenge. In this Example, the MAP burden in these organs was assessed to gauge the protective efficacy of Map74F following challenge. It is evident from the results presented below that Map74F immunized animals were able to either kill or inhibit the proliferation of MAP over a 16 weeks course of infection. In spleen, liver and MLN, the number of CFU decreased at 8 weeks after challenge, suggesting MAP elimination. Apart from the bacterial burden, the reduced number of granulomas and fewer acid-fast organisms observed in the liver and spleen of vaccinated animals indicated the protective efficacy of the polyprotein. The substantially reduced MAP load in the organs and the improved liver and spleen pathology indicate that immunization with 74F protected mice against MAP infection by rapidly decreasing or eliminating MAP load. Map74F also elicits high levels of IFN-γ. Map74F induced a good Th1 response.

The following materials and methods were used in this Example.

Animals

Experiments were performed using 6-8 week old female C57/BL6 mice (Harlan Sprague, Indianapolis, Ind.). Animals were maintained in a biosafety level II facility and had free access to feed and water. All the experimental work was conducted in compliance with the regulations, policies, and principles of the Animal Welfare Act, the Public Health Service Policy on Humane Care and Use of Laboratory Animals used in Testing, Research, and Training, the NIH Guide for the Care and Use of Laboratory Animals and the New York State Department of Public Health.

Bacterial Strain

A MAP isolate from an infected cow, designated MAP 66115-98, was used to challenge the mice and for isolation of genomic DNA. MAP 66115-98 was grown in 7H9 medium supplemented with 10% oleic acid-albumin-dextrose-catalase (Becton, Dickinson and Co, Sparks, Md.) and mycobactin J (Allied Monitor, Inc, Fayette, Mo.). After culturing for 6-8 weeks, organisms were harvested by centrifugation at 10,000×g and washed twice with phosphate buffered saline (PBS; pH 7.2). The organisms were diluted in PBS to the required concentration and used for challenging the mice.

Immunization of Mice

Mice were divided into two groups with 36 animals in each group. Group I animals were immunized twice, three weeks apart with 50 μg/animal, of the fusion protein formulated with MPL+TDM Emulsion (Ribi adjuvant systems, Corixa, Hamilton, Mont.) in a total volume of 100 μl per dose via subcutaneous injection on the back. Group II animals were kept as unvaccinated controls and administered MPL+TDM Emulsion alone. Three weeks after the second immunization, 12 animals in each group, designated for immunogenicity studies, were killed and spleen cells were obtained by conventional procedures. Spleen cells were cultured in RPMI 1640 medium (Gibco, Grand Island, N.Y.) containing 10% FBS (Gibco) at 37° C. at 5% CO2. Immunization experiments were repeated twice with the same dose and schedule.

Challenge of Mice with MAP

Three weeks after the second immunization, 24 animals each in Group I and II were challenged by intraperitoneal injection of $10^9$ CFU units of *Mycobacterium avium* subsp. *paratuberculosis*. Six animals each in both groups were euthanized at 4, 8, 12 and 16 weeks after the challenge and spleen, liver and mesenteric lymph nodes (MLN) were collected and divided into two parts. One set of tissues was homogenized in PBS (100 mg/ml) and 100 µl of individual tissue homogenates were inoculated on to Herald's egg yolk (HEY) slants (Becton, Dickinson and Co, Sparks, Md.) containing mycobactin J. in order to estimate the bacterial load. The slants were checked for bacterial growth by colony count after 8-12 weeks of inoculation. The other set of tissues was used for histopathological examination.

Histopathological Examination

Portions of spleen, liver and MLN were fixed by immersion in 10% neutral buffered formalin, embedded in paraffin wax, sectioned at 4 µm and stained with hematoxylin and eosin and Ziehl-Neelsen stain by conventional histological methods and examined by light microscopy.

ELISA for Antibody Response

Antigen specific IgG response was measured by conventional ELISA. ELISA plates (Nunc-immuno module, Nunc, Roskilde, Denmark) were coated with 200 ng/well of recombinant protein and incubated at 4° C. overnight. After washing once with PBST (0.05% Tween 20 in PBS), 300 µl of blocking buffer (1% BSA in PBST) was added and incubated at 25° C. for 1 hour. The plates were washed 3 times with PBST and 100 µl of diluted serum samples were added to the wells and incubated at 37° C. for 1 hour. For total IgG response, after washing, 50 ng of alkaline phosphatase conjugated goat anti-mouse IgG (KPL, Gaithersburg, Md.) was added to the wells and incubated at 25° C. for 30 minutes. After washing, 50 µl of BluePhos substrate (KPL) was added and incubated for 10 minutes. Plates were read in an $EL_x$ 808 Ultra microplate reader (Bio-Tek Instruments, Inc, Winooski, Vt.) at 630 nm after adding 50 µl of stop solution (KPL). For isotype response, after washing, 25 ng of biotin conjugated goat anti-mouse IgG1 or IgG2a (Southern Biotech, Birmingham, Ala.) was added to the wells and incubated at 25° C. for 30 minutes. After washing, 0.2 µg/ml of streptavidin labeled with horseradish peroxidase (KPL) was added and incubated at 25° C. for 30 minutes. After washing, 50 µl of 3,3', 5,5'-Tetramethylbenzidine (TMB) was added to the wells and incubated for 15 minutes. Plates were read in an $EL_x$ 808 Ultra microplate reader (Bio-Tek Instruments) by endpoint method at 450 nm after adding 50 µl of 1N $H_2SO_4$ as stop solution.

IFN-γ Assay

Spleen cells obtained by conventional procedures were plated in duplicate at $5 \times 10^5$ cells/well and cultured with and without the recombinant antigen for 48 h. Culture supernatants were harvested and analyzed for IFN-γ using a solid phase sandwich ELISA kit (Biosource, Camarillo, Calif.) according to the manufacturer's protocol. Briefly, 50 µl of culture supernatants were added to the wells coated with monoclonal antibody specific for mice IFN-γ. After 2 hr co-incubation at room temperature with biotinylated polyclonal antibody, the wells were washed and streptavidin-peroxidase was added. After 30 min incubation and washing, tetramethylbenzidine (TMB) solution was added to the wells and the results were read at 450 nm in $EL_x$ 808 Ultra microplate reader (Bio-Tek Instruments).

ELIspot Assay

An ELIspot kit (KPL) was used to determine the relative number of IFN-γ expressing cells in the single-cell spleen suspensions according to the manufacturer's instructions. Briefly, 10 µg/ml of IFN-γ capture Ab (BD Biosciences, San Jose, Calif.) was coated onto the MultiScreen 96-well filter plate (Millipore, Bedford, Mass.) for overnight at 4° C. After washing with 1× washing solution, plates were blocked by 1×BSA solution for 1 hour at 25° C. and washed again. Spleen cells were plated in duplicate at $5 \times 10^5$ cells/well and cultured with and without the antigen for 48 hours at 37° C. The plates were washed with 1× washing solution and incubated 1 hr at 25° C. with 5 µg/ml biotin conjugated rat anti-mouse IFN-γ secondary Ab (BD Biosciences). The plates were washed and incubated for 30 min at 25° C. with 0.2 µg/ml of HRP-streptavidin. The filters were developed by TureBlue substrate for 15 minutes, dried in the dark and the spots were counted.

FACS Analysis for Cell Surface Markers

Spleen cells were plated in duplicate in 96-well tissue culture plates at $1 \times 10^6$ cells/well and cultured for 24 hr. FACS analysis was preformed after stimulating the spleen cells with 74F and concanavalin A with suitable unstimulated control cells. After washing thrice in FACS buffer (1% BSA and 0.05% sodium azide in PBS), the cells were suspended in 50 µl of FACS buffer and mixed with 0.5 µg of FITC or PE conjugated CD3, CD4 and CD8 antibodies (eBioscience, San Diego, Calif.) and incubated on ice for 30 minutes. Cells were washed with FACS buffer twice and suspended in 100 µl of 3% formaldehyde in PBS and transferred to FACS tubes containing 500 µl of PBS. Data were collected on 10,000 events using a FACS caliber flow cytometer (Becton-Dickinson, San Jose, Calif.) and analyzed using Cellquest software. The results were expressed as the increased average percentage of cells with positive staining relative to that of the uninduced sample stained with the same antibody.

Real-Time RT-PCR for Cytokine mRNA Expression

Total RNA was isolated from the splenic tissues of immunized mice using RNeasy mini kit (Qiagen, Valencia, Calif.). Messenger RNA was reverse-transcribed using Super-Script™ II (Invitrogen) and used as template cDNA. The details of primer and probe sequences used are presented in Table. 1. The following annotations are used in Table 1: FW, forward primer; RV, reverse primer; TP, TaqMan probe, dual-labeled with 5'FAM and 3'TAMRA; [a]Amplicon length in base pairs. [b]Genbank accession number of cDNA and corresponding gene. [c]Antisense probe.

The probes were labeled with the fluorescent reporter dye, 6-Carboxyfluorescein (FAM) at the 5'end and the quencher dye, N', N',N',N',N'-6-Carboxytetramethylrhodamine (TAMRA) at the 3' end. The reaction was performed in duplicate in 25 µl volumes containing 2 µl of 10 pM forward and reverse primers, 2 µl of 2 pM probe, 12.5 µl of TaqMan PCR master Mix and 9.5 µl of diluted cDNA, using the following conditions: 10 min at 94° C., followed by a total of 40 two-temperature cycles (15 seconds at 95° C. and 1 min at 60° C.), in an automated fluorometer (7700 Sequence detector, Applied Biosystems, Foster city, Calif.). Quantitation was done using the comparative cycle threshold ($C_T$) method and reported as relative transcription or the n-fold difference relative to a calibrator cDNA.

TABLE 1

| Gene | Sequence (5'→3') | Length (bp)[a] | Accession No.[b] |
| --- | --- | --- | --- |
| IL-2 | FW CCTGAGCAGGATGGAGAATTACA (SEQ ID NO: 10) | 141 | X017722 M16760 |

TABLE 1-continued

| Gene | Sequence (5'→3') | Length (bp)[a] | Accession No.[b] |
|---|---|---|---|
| | RV TCCAGAACATGCCGCAGAG (SEQ ID NO: 11) | | AF195956 |
| | TP CCCAAGCAGGCCACAGAATTGAAAG (SEQ ID NO: 12) | | |
| IL-12p40 | FW GGAAGCACGGCAGCAGAATA (SEQ ID NO: 13) | 180 | M866712 S82420-6 |
| | RV AACTFGAGGGAGAAGTAGGAATGG (SEQ ID NO: 14) | | |
| | TP CATCATCAAACCAGACCCGCCCAA (SEQ ID NO: 15) | | |
| TNF-α | FW CATCTFCTCAAAATTCGAGTGACAA (SEQ ID NO: 16) | 175 | M130492 Y00467 |
| | RV TGGGAGTAGACAAGGTACAACCC (SEQ ID NO:17) | | |
| | TP CACGTCGTAGCAAACCACCAAGTGGA (SEQ ID NO: 18) | | |
| INF-γ | FW TCAAGTGGCATAGATGTGGAAGAA (SEQ ID NO: 19) | 92 | K00832 M74466 M28381 |
| | RV TGGCTCTGCAGGATTTTCATG (SEQ ID NO: 20) | | |
| | TP[c] TCACCATGCTTTTGCCAGTTCCTCCAG (SEQ ID NO: 21) | | |
| GAPDH | FW TCACCACCATGGAGAAGGC (SEQ ID NO: 22) | 168 | M325991 U09964 |
| | RN GCTAAGCAGTTGGTGGTGCA (SEQ ID NO: 23) | | |
| | TP ATGCCCCCATGTTTGTGATGGGTGT (SEQ ID NO: 24) | | |

Statistical Analysis

The data were statistically analyzed with Excel software. Differences between groups and individual antigens were analyzed with one-way analysis of variance followed by Tukey-Kramer multiple comparison or Student's t-test. Differences were considered significant when a probability value of <0.05 was obtained.

The following results were obtained using the materials and methods set forth in this Example.

Immune Response in Mice Immunized with Map 74F Protein

Three weeks after booster vaccination, four mice from each group were killed, and anti-Map74F antibody response and T cell response were evaluated. Mice immunized with Map 74F had a significantly (P<0.01) stronger IgG1 response against Map 74F but not IgG2a. In contrast, no Map 74F-specific antibodies were detected in the control group.

IFN-γ responses were assessed by IFN-γ ELISA of the culture supernatant and the IFN-γ ELISPOT assay. Antigen specific IFN-γ response was significantly higher (P<0.05) in mice immunized with Map 74F as compared to the control animals which received MPL alone (FIG. 2A). IFN-γ ELISPOT result was also comparable to the IFN-γ ELISA result (FIG. 2B), which further confirmed the increased IFN-γ response in the vaccinated animals. The vaccinated group had a mean single-cell forming colonies (SFC) of 20, in contrast to 7 in the control group. Distribution of antigen specific CD3+, CD4+, and CD8+T cells in spleen cells were evaluated by FACS. CD3+ and CD4+T cells were significantly higher (P<0.01) in mice immunized with Map 74F (FIG. 2C) than the control animals. In contrast, no significant difference was seen in CD8+T cell populations between vaccinated and control animals. Cytokine gene expression levels were evaluated by real-time PCR. No significant differences (P>0.05) were detected in the expression levels of the cytokine genes IL-2, IL-12, TNF-α and IFN-γ between the vaccinated and control animals (FIG. 2D).

Map 74F Protects C57/BL6 Mice Against MAP Infection

Based on the immune responses obtained in vaccinated mice, we planned to assess the protective efficacy of Map 74F protein against MAP infection in mice. The sera collected at different time points were tested by ELISA for total IgG response (FIG. 3A) and IgG1/IgG2a ratio (FIG. 3B). Mice immunized with 74F showed a significant (P<0.01) increase in 74F specific antibody response at 3 and 7 weeks (4 weeks after challenge) after the booster vaccination compared to the control animals. Although the antibody levels increased in the control animals following challenge, the response was higher in the vaccinated animals at 8, 12 and 16 weeks after challenge. Significant differences were detected in the IgG1/IgG2a ratios of vaccinated and control animals by 3 wk after the booster vaccination. In the vaccinated animals the IgG1/IgG2a ratios increased after booster vaccination until 4 wk after challenge. Thereafter, a drop in the IgG1/IgG2a ratios was noticed in the vaccinated animals until the end of the observation period 16 wk post-challenge.

Figure 4C:
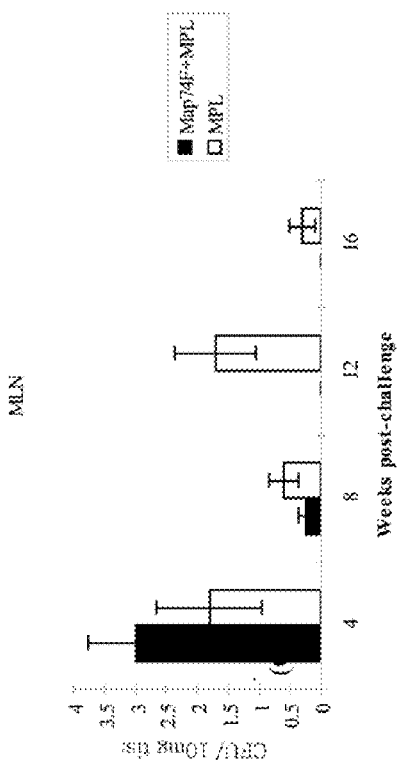

To assess the protective efficacy of 74F, spleen, liver and MLN were cultured for MAP at different time points following challenge with MAP. In the spleen, MAP burden was significantly (P<0.01) lower in the vaccinated animals compared to the control animals at 8, 12 and 16 weeks after challenge (FIG. 4A). In the liver, vaccinated animals had a lower MAP burden than the control animals and the burden was significantly (P<0.01) lower at 12 weeks after challenge (FIG. 4B). In vaccinated animals, MAP burden in the MLN was significantly lower from 8 weeks on after challenge (FIG. 4C). Histopathological examination of liver (FIG. 5. A &B) and spleen (FIG. 5. C&D.) showed that intra-peritoneal challenge of MAP resulted in more granulomas in the control animals at 8, 12 and 16 weeks post-challenge. In the un-vaccinated control animals, the liver had numerous large randomly dispersed granulomas (FIG. 5A) while the liver of the vaccinated animals had only sparse numbers of small lymphoid aggregates (FIG. 5B). Similarly, spleen of un-vaccinated control animals had more granulomas (FIG. 5. C) than the vaccinated animals (FIG. 5.D). When the liver and spleen tissues from control animals were stained with Ziehl-Neilsen, numerous acid-fast bacilli were seen. In contrast, the number of granulomas and acid-fast bacilli were fewer in animals immunized with 74F.

Thus, in this Example, we used spleen cells from vaccinated and control animals to ascertain the type of T cell response induced by the fusion protein. In mycobacterial infections, Th1 cells are crucial for protection during the early phase of the infection. The most effective vaccination strategies against intracellular pathogens are considered to be those that stimulate both CD4$^+$ and CD8$^+$T cell responses to produce Th1-associated cytokines. In general, IFN-γ is regarded as the major component in activation of macrophages and its production by Th1 CD4$^+$ T cells is considered essential for containing MAP infection Our results indicate that vaccination with the fusion protein elicited a significant IFN-γ response. Similarly, we also found that immunization with Map74F elicited a strong CD3$^+$ and CD4$^+$ T cell response in the vaccinated animals in contrast to the CD8$^+$ T cells, indicating that the increase in IFN-γ levels could be due to the increase in CD4$^+$ T cell populations. The results support the conclusion that the expression of IFN-γ was predominantly by activated CD4$^+$ T cells. The increased CD4$^+$T cell response and the protection levels obtained in our study following MAP challenge indicate the protective efficacy of Map74F.

Our immunogenicity studies presented in this Example also indicate that 74F with MPL induced a good antibody response in the vaccinated animals. The IgG1/IgG2a ratio increased until 4 wk after MAP challenge, indicating a Th2 specific response. However, the IgG1/IgG2a ratio decreased gradually beginning at 8 wk indicating a possible shift to Th1 response. It is evident from the results presented in this Example that 74F induced both Th1 and Th2 responses with the former being more pronounced as exhibited by a significant IFN-γ response.

Example 3

This Example demonstrates the use of Map74F and other selected MPA proteins to simulate an immune response against MAP in ruminants.

The following materials and methods were used to obtain the data presented in this Example.

Animals. A total of 25 goat kids, between 5 and 10 days of age, from herds free from MAP were used in this study. Fecal samples taken from the goats before the immunization experiments were negative for MAP, both by culture and by PCR for the IS900 gene. All of the experimental work was conducted in compliance with the regulations, policies, and principles of the Animal Welfare Act, the Public Health Service Policy on Humane Care and Use of Laboratory Animals used in Testing, Research, and Training, the NIH Guide for the Care and Use of Laboratory Animals and the New York State Department of Public Health.

Bacteria. MAP 66115-98, a clinical isolate, was used to challenge the goats after immunization. This strain is IS900 positive and mycobactin dependent. MAP 66115-98 was grown in 7H9 medium supplemented with 10% oleic acid-albumin-dextrose-catalase (Becton Dickinson Co, Sparks, Md.) and mycobactin J (Allied Monitor, Inc, Fayette, Mo.). After culturing for 8 weeks, the organisms were harvested by centrifugation at 4000×g for 10 min and washed twice with phosphate buffered saline (PBS; pH 7.2). The organisms were diluted in PBS to the required concentration and used for challenging the calves.

Antigens and adjuvant. Three recombinant MAP antigens, 85A, 85B, SOD, and the fusion polypeptide Map74F were cloned, expressed, and purified using standard techniques and as set forth in U.S. application Ser. No., 11/816,365, the description of which cloning, expression and purification is hereby incorporated by reference. The expressed proteins were purified using Ni-NTA agarose columns (Qiagen, Valencia, Calif.). Endotoxin contamination was removed by use of Affinity Pak Detoxi Gel (Pierce, Rockford, Ill.) and the antigens had negligible levels (10 pg/ml) of endotoxin in a Limulus amoebocyte assay. DDA (Sigma, USA) was mixed in sterile distilled water to a concentration of 2.5 mg/ml, heated to 80° C. with constant stirring for 20 min and cooled to room temperature. DDA was mixed thoroughly with the recombinant antigens to a final concentration of 250 μg/dose.

Immunization of animals. The goats were divided into three groups, with eight animals in group I and II and 9 animals in Group III (since we had an extra goat kid). All goat kids stayed with their dams until three months of age. Group I animals were immunized with 100 μg each of the four antigens (85A, 85B, SOD, and Map74F) in DDA by subcutaneous injection. Group II animals were immunized with 100 μg of each antigen without DDA. Group III were kept as control animals and administered only DDA. Three weeks after the primary immunization, the goats were boosted with the same regimen of antigens and adjuvant.

Challenge of animals with MAP. Three weeks after the booster, all 24 goats were challenged orally with 5×10$^8$ MAP cells/animal in 10 ml milk replacer for 7 consecutive days. Fecal cultures were performed on each animal on days 2, 4, 6, 8 and 10 after each challenge and then once every month.

Isolation and culturing of peripheral blood mononuclear cells (PBMC). PBMC were isolated from the experimental goats using standard techniques. Briefly, 10-15 ml of peripheral blood was collected from the jugular vein into EDTA vacutainer tubes (Becton Dickinson and Co, Franklin Lakes, N.J.). Lymphocytes were isolated by differential centrifugation using Histopaque 1.077 (Sigma-Aldrich, St. Louis, Mo.). The mononuclear cells were washed three times with phosphate-buffered saline (PBS, pH 7.2). Washed cell pellets were suspended in PBS and counted after staining with 0.4% trypan blue for viability. The lymphocytes were resuspended in RPMI-1640 medium containing 10% fetal bovine serum (Gibco, Grand Island, N.Y.), 2 mM L-glutamine, 100 mM HEPES, 100 IU/ml of penicillin, 100 μg/ml of streptomycin and 50 μg/ml of gentamycin (Gibco), to a final concentration of 2×10$^6$ viable cells/ml. The cells were seeded (200 μl/well) onto 96-well round or flat bottom plates, depending on the type of experiment.

Lymphocyte proliferation assay. Lymphocyte proliferation assays were performed using standard techniques. Briefly, PBMC, in 96-well flat bottom plates were incubated at 37° C. in a humidified atmosphere in 5% $CO_2$ and stimulated with each of the four purified recombinant antigens (10 μg/ml), concanavalin A (ConA; 10 μg/ml, Sigma-Aldrich, St. Louis, Mo.) and purified protein derivative (PPD; 10 μg/ml, DBL, National Veterinary Services Laboratory, Ames, Iowa) for 72 hr. DNA synthesis in stimulated and un-stimulated control cells was measured by the incorporation of bromodeoxyuridine (BrdU) by Cell proliferation ELISA, BrdU colorimetric kit (Roche Diagnostics, Indianapolis, Ind.) as per the manufacturer's protocol. Briefly, the cells were labeled for 2 hr with 10 μl of BrdU labeling solution. The peroxidase conjugated anti-BrdU antibody was added and incubated for 90 min. This was followed by the addition of the enzyme substrate solution and incubation at room temperature for 15 min. The enzymatic reaction was stopped by the addition of 1 M $H_2SO_4$, and the optical density (OD) was read at 450 nm using an $EL_x$ 808 Ultra microplate reader (Bio-Tek Instruments, Inc, Winooski, Vt.). The tests were run in triplicate, and the results were expressed as the average stimulation index (SI), calculated as the ratio between the mean OD of cells cultured with the antigens and the mean OD of cells cultured without the antigens.

IFN-γ assay. IFN-γ levels were measured in the culture supernatants of PBMC using a monoclonal antibody-based sandwich enzyme immunoassay (BOVIGAM; Biocor Animal Health, Omaha, Nebr.), as per the manufacturer's instructions. The plates were read at 450 nm using an ELx 808 Ultra microplate reader (Bio-Tek Instruments, Inc). The results were interpreted based on a comparison of negative and positive control optical density (OD). Results were determined as either positive (if the OD is more than that of positive control) or negative (if the OD is less than that of positive control), relative to the cutoff values as suggested by the manufacturer.

Flow cytometric analysis of lymphocyte markers. Single-color flow cytometric analysis was performed for lymphocyte surface differentiation antigens, using goat-specific monoclonal antibodies (CD2-MUC2A; CD4-17D-IgG$_1$; CD4-GC1A1-IgG2a; CD8-CACT80C-IgG$_1$; CD8-7C2B-IgG2$_a$; CD25-CACT116A-IgG$_1$; CD45RO-ILA116A-IgG3; γδTCR alpha chain specific IgG2b-GB21A1; ACT1-CACT7A-IgM; ACT16-GB110A-IgM) (VMRD, Inc, Pullman, Wash.) according to standard protocols. Briefly, the cells were washed three times in fluorescence activated cell sorter (FACS) buffer and incubated with the primary antibody previously titrated for optimum reactivity for 30 min at 4° C. Following this, the samples were washed three times and incubated with fluorescein isothiocyanate labeled horse anti-mouse immunoglobulin (Vector Laboratories, Burlingame, Calif.) for 30 min at 4° C. The cells were washed twice in FACS buffer and suspended in 100 µl of 3% neutral buffered formalin in PBS. Finally, the cells were transferred to a FACS tube, and the volume was made up to 500 µl with PBS prior to measurement using a FACS caliber flow cytometer (Becton Dickinson, San Jose, Calif.). Data was collected on 5,000-10,000 events and were analyzed using Cellquest software.

Real-time quantitative PCR for cytokine gene expression. Total RNA isolation, cDNA synthesis, and real-time quantitative RT-PCR were performed according to conventional methods. Briefly, RNA was isolated from lysed PBMC using an RNeasy mini Kit (Qiagen, Valencia, Calif.). The isolated RNA samples were treated with 10 U/µl of RNase-free DNase I (Qiagen) at 37° C. for 10 min, followed by heat inactivation at 95° C. for 5 min and then chilled on ice. Reverse transcription of the RNA samples was carried out in a 20 µl reaction volume (1.6 µl of total RNA, 200 U of Superscript II reverse transcriptase from Invitrogen, 50 mM Tris-HCl, 75 mM KCl, 3 mM $MgCl_2$, 0.01 M dithiothreitol and 0.5 mM dNTPs) at 42° C. for 50 min, followed by inactivation at 70° C. for 15 min. Probes and primers for real-time quantitative RT-PCR were designed with Primer Express software (Applied Biosystems, Foster city, Calif.) using bovine beta actin and cytokine gene sequences derived from GenBank. The details of probes and primers used in this study are presented in Table 2.

TABLE 2

| Cytokine | Sequence (5'→3') | Length | Accession No. |
|---|---|---|---|
| IFN-γ | FP-CAAATTCCGGTGGATGATCTG (SEQ ID NO: 25) | 358-378 | AY603405 |
|  | RP-GCGACAGGTCAUCATCACCTT (SEQ ID NO: 26) | 433-412 |  |
|  | Probe-atccagcgcaaagccataaatgaactca (SEQ ID NO: 27) | 382-409 |  |
| IL-10 | FP-CCAGGATGGTGACTCGACTAGAC (SEQ ID NO: 28) | 338-360 | DQ837I59 |
|  | RP-TGGGTCTGGTCTCCCAGAAC (SEQ ID NO: 29) | 413-394 |  |
|  | Probe-ccgacataaacctctgaaatccgaccca (SEQ ID NO: 30) | 364-391 |  |
| β-actin | FP-GGCCCTCTGAACCCCAAA (SEQ ID NO: 31) | 67-84 | AF481159 |
|  | RP-GCAGGAGTGTTGAAAGTCTCGAA (SEQ ID NO: 32) | 137-115 |  |
|  | Probe-ccaaccgtgagaagatgacccagatca (SEQ ID NO: 33) | 86-112 |  |

The probes were labeled with the fluorescent reporter dye, 6-carboxyfluorescein (FAM) at the 5'end, and the quencher dye, N', N', N',N',N'-6-carboxytetramethylrhodamine (TAMRA) at the 3' end. PCR was performed in a 25 µl reaction volume with 10 µl of diluted cDNA, 400 nM concentrations of primers, 80 nM of TaqMan probe (Integrated DNA Technologies, Inc., Coralville, IO), and universal PCR master mix (Applied Biosystems), containing 10 mM Tris-HCl (pH 8.3), 50 mM KCl, 5 mM $MgCl_2$, 2.5 mM concentrations of deoxynucleotide triphosphates, 0.625 U AmpliTaq Gold DNA polymerase and 0.25 U AmpErase uracil-N-glycosylase per reaction. Duplicate samples were kept in 96-well plates and amplified in an automated fluorometer (7700 Sequence Detector, Applied Biosystems). The PCR conditions were 2 min at 50° C. and 10 min at 95° C., followed by 40 cycles at 95° C. for 15 sec and 60° C. for 1 min. Quantitation was done using the comparative cycle threshold ($C_T$) method and reported as relative transcription or the n-fold difference relative to a calibrator cDNA.

Antibody responses to recombinant antigens. Antibody responses to the four recombinant antigens, con A and PPD were estimated by ELISA following a conventional protocol. An indirect ELISA was performed with 96-well flat bottom plates coated with 100 µl of each antigen, kept at 4° C. overnight, and washed three times with PBS containing 0.05% Tween 20 (PBST). Unbound sites were blocked with 5% skim milk in PBST at 37° C. for one hr and washed twice with PBST. 100 μl of 1:25,000 diluted anti-goat IgG-conjugated with horseradish peroxidase (Sigma) were added to the wells and incubated at 37° C. for one hr. The plates were washed three times in PBST and 200 μl of 2,2'-azinobis-thiazoline-6-sulfonic acid (Sigma) was added to each well. Plates were incubated at 37° C. for 30 min in the dark followed by the addition of stop solution (1 M HCl), and read three times at 405 nm at 2 min intervals using a microplate reader (BioTEK Instruments, Inc, Winooski, Vt.). Suitable positive and negative sera and antigen and antibody controls-were included in each plate.

Fecal and organ culture of MAP. Following challenge, attempts were made to isolate MAP organisms from feces using Herald's egg yolk (HEY) medium (Becton, Dickinson and Co. Sparks, Md.) following standard protocols. Fecal samples were collected from all animals at 2, 4, 6, 8 and 10 days after challenge, and every month thereafter for MAP isolation. Similarly, 23 tissue samples collected from each of the 24 animals at necropsy were also tested for MAP by culture. Cultures were performed by the Bacteriology section at the Cornell Animal Health Diagnostic center, and they were blinded to the treatment group.

Gross pathology and histopathological examination. All the goats were euthanized 38 wk after primary vaccination and necropsied. A total of 23 tissue samples from each animal, which included spleen, tonsils, mesenteric lymph nodes (3), mandibular lymph node, ileo-cecal lymph node, hepatic lymph node, duodenum (ascending and descending), jejunum (3 sites of approximately equal intervals from proximal to distal end), ileum (2 sites at proximal end, 2 sites at mid ileum and 2 sites at distal end), ileo-cecal orifice, cecocolic orifice, cecum, and spiral colon were collected at the time of necropsy. Collected tissues were fixed by immersion in 10% neutral buffered formalin, embedded in paraffin wax, sectioned at 4 μm and stained with hematoxylin and eosin by conventional histological methods. Sections were examined by a board certified veterinary pathologist (SM), who was blinded to the treatment group.

Statistical analysis. The data were statistically analyzed with the Excel software. Differences between groups and individual antigens were analyzed with one-way analysis of variance followed by Tukey-Kramer multiple comparison or Student's t-test. Differences were considered significant when a probability value of <0.05 was obtained.

The following results were obtained using the materials and methods set forth above in this Example.

Lymphoproliferative responses to the antigens: Although antigen specific lymphoproliferative responses were detected at 6 wk after primary vaccination (APV), the responses were significantly higher (P<0.05) in both vaccinated groups (I and II) compared to the unvaccinated control group (III) at 10 wk APV (FIG. 6). Nevertheless, no significant differences were detected in the responses between the different antigens tested.

Antigen specific IFN-γ responses: Significant differences (P<0.01) were detected in the IFN-γ responses between the vaccinated and control animals at 6 and 10 wk APV (FIG. 7). In the vaccinated animals the best response was detected for Map74F. IFN-γ responses were significantly higher (P<0.05) for antigens 85A and Map74F in group I animals than group II animals at 10 wk APV. However, no significant differences were detected among the other recombinant antigens tested. Though the recombinant antigen specific IFN-γ levels declined from 18 wk through 38 wk APV, they were significantly higher (P<0.05) in the vaccinated animals than the controls.

Figure 8A:
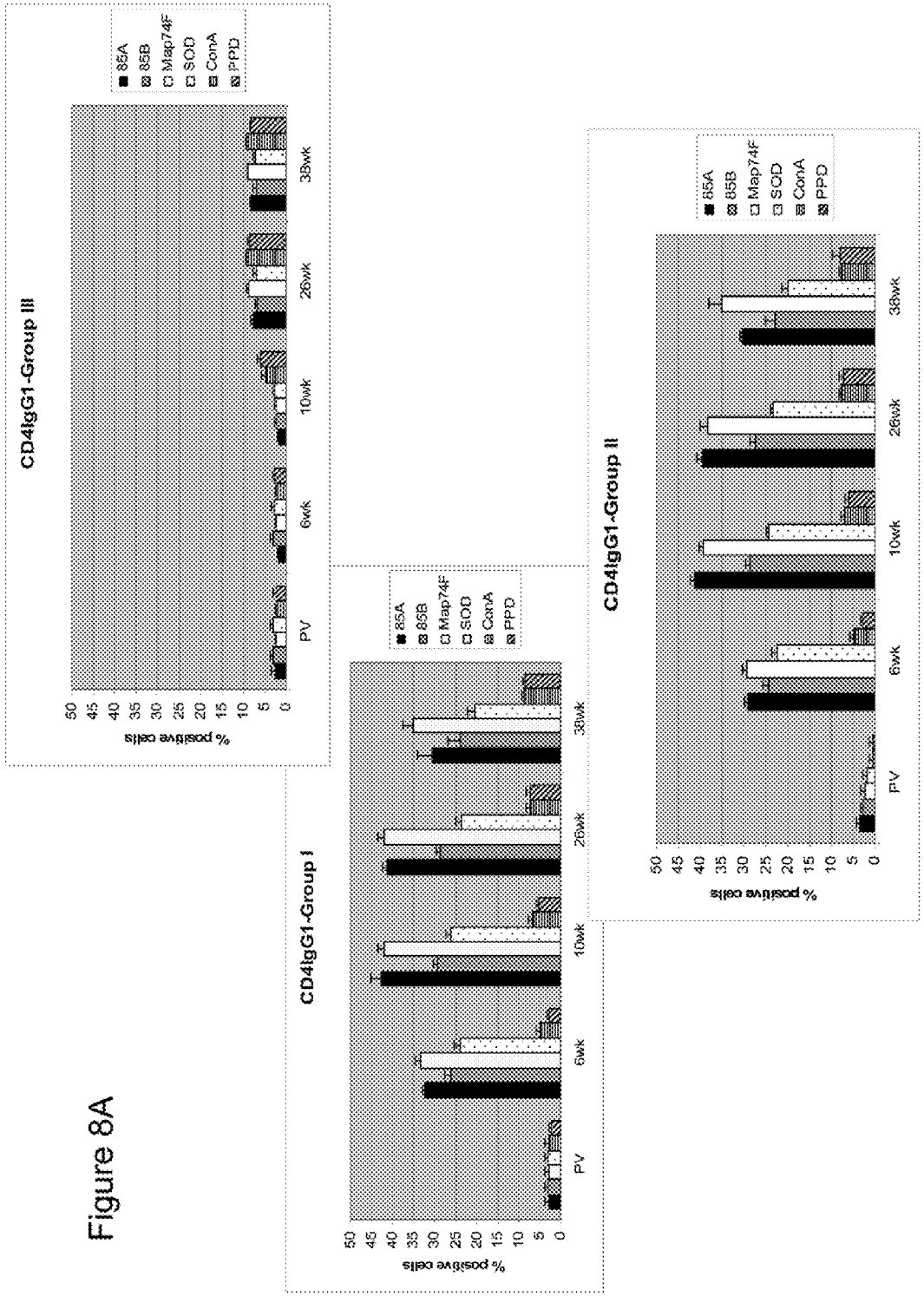
Figure 8B:
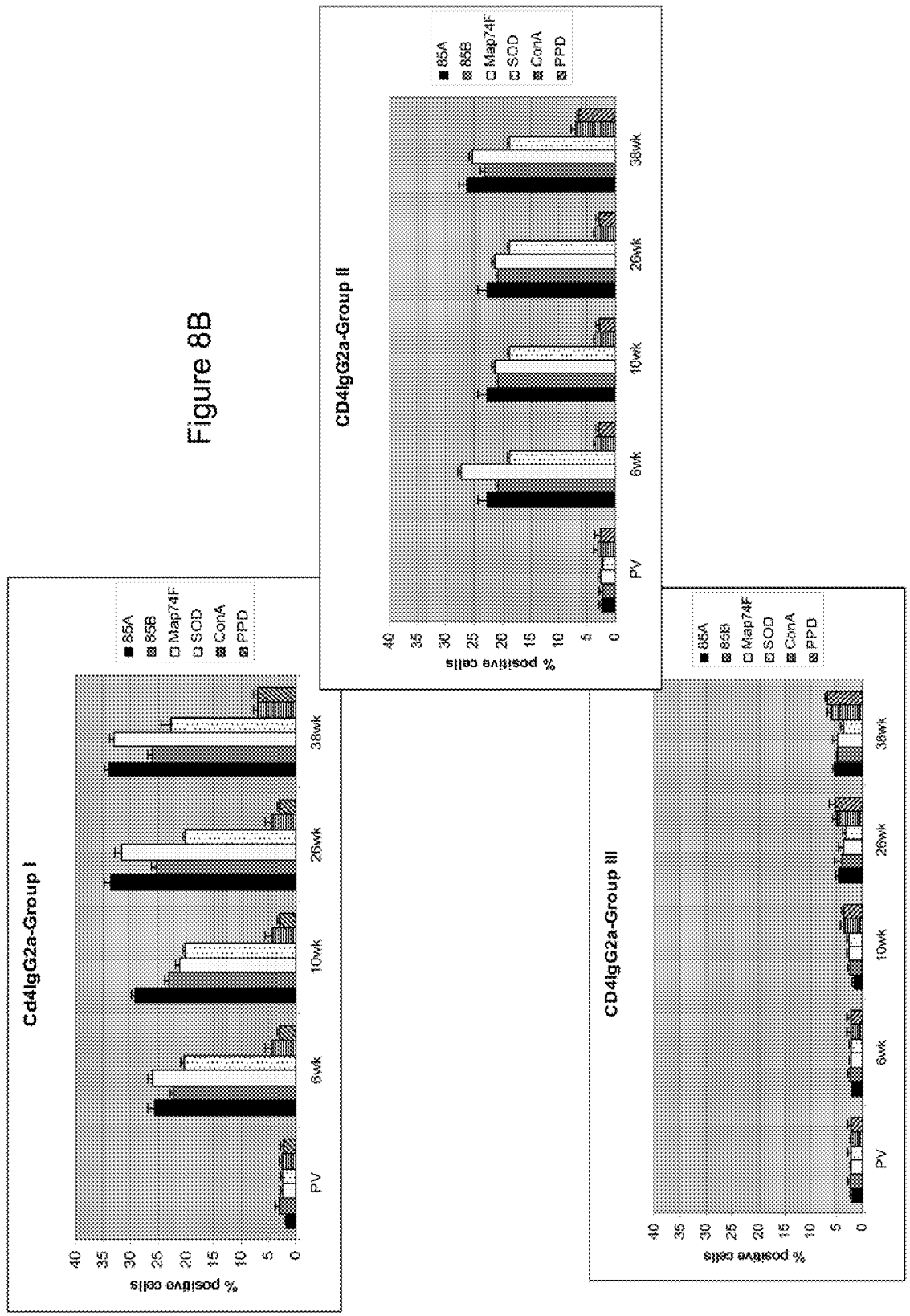
Figure 8D:
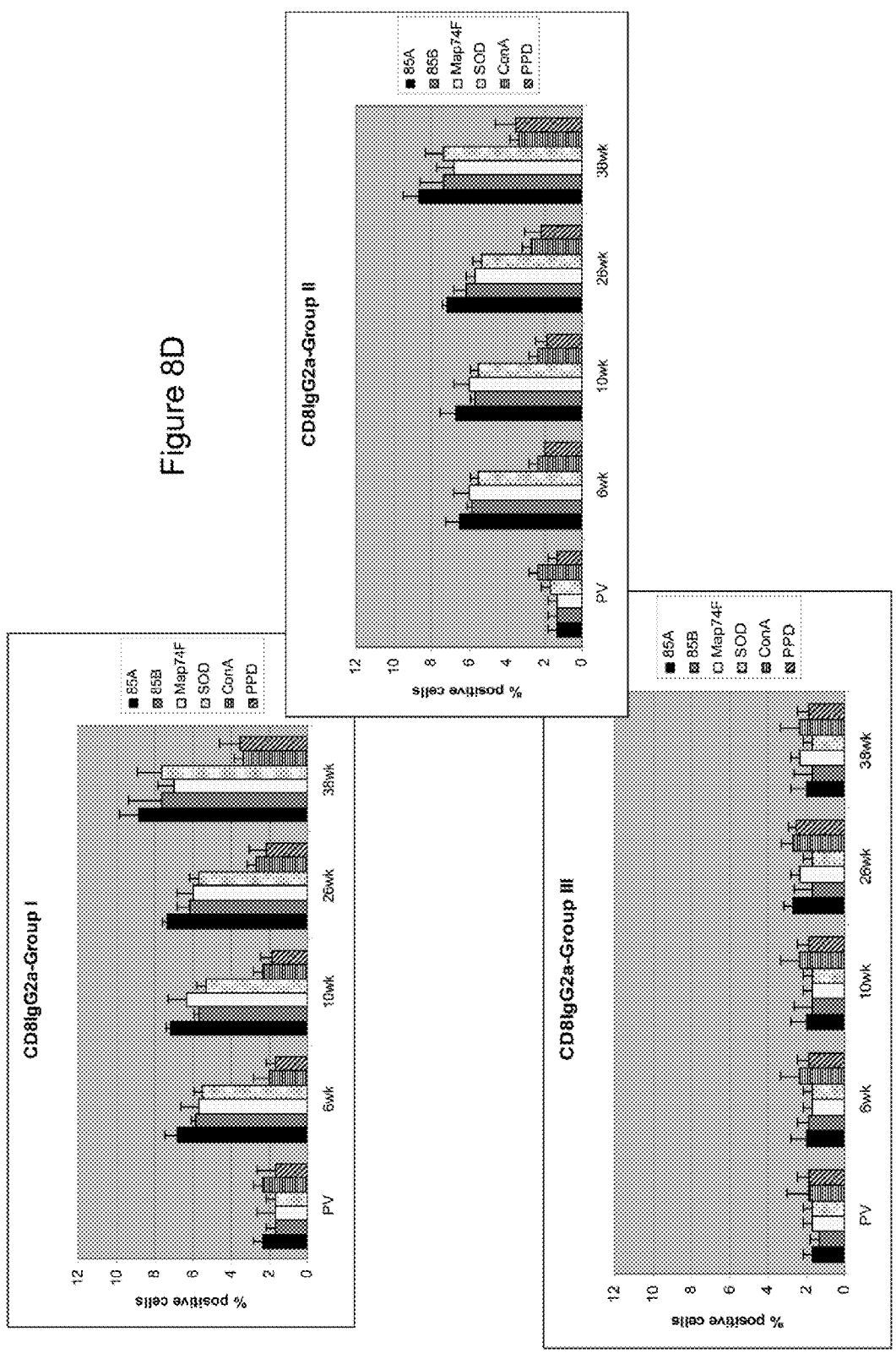
Figure 8F:
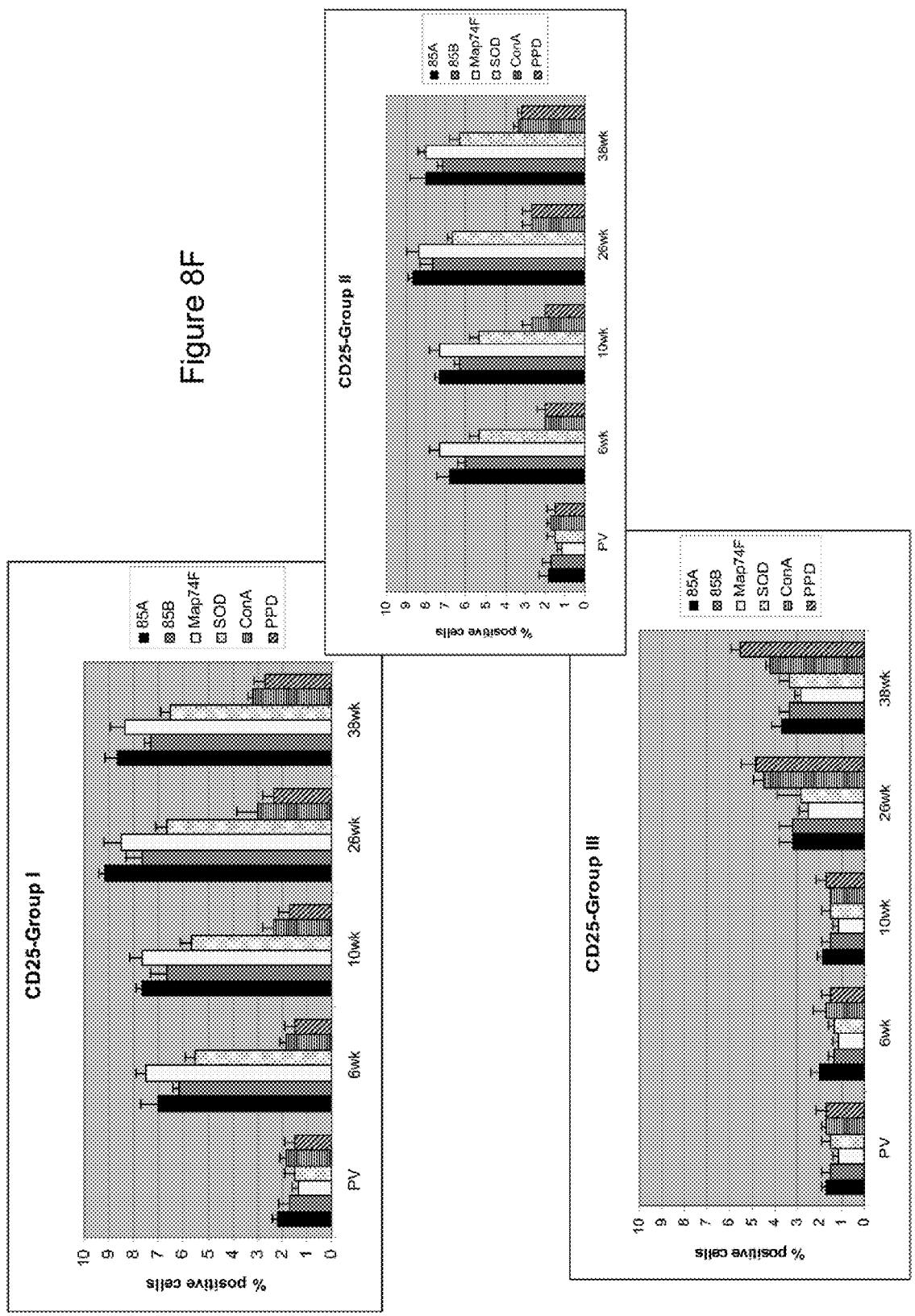

Lymphocyte subset distribution in response to recombinant antigens: Antigen stimulated lymphocyte subsets were examined for differences in their percentages by flow cytometry. There were significant (P<0.01) increases in $CD4^+IgG1$, $CD4^+IgG2a$, $CD8^+IgG1$, $CD8^+IgG2a$ cell subtypes in the immunized groups over the control group (FIG. 8A-D). The increase began at 6 wk APV and persisted throughout the entire experiment period to 38 wk APV. Recombinant antigen specific $CD4^+$ and $CD8^+$ T cell populations were higher in the immunized animals, but the proportion of $CD4^+$ cells was higher than that of $CD8^+$ cells. However, there was an increase, though not significant, in the $CD8^+$ T cell population at 26 and 38 wk APV. While all the recombinant antigens tested in our study increased the $\gamma\delta TCR^+$ cell populations in both the vaccinated groups compared to the control animals, the increase was significantly (P<0.05) higher for 85A and Map74F antigens. Again, as in the case of $CD4^+$ and $CD8^+$ T cell populations, a sustained increase in $\gamma\delta TCR^+$ cell populations was noticed until the end of the experimental period (FIG. 8E). In the immunized animals, the proportion of antigen specific $CD25^+$ T cells were higher for the four recombinant antigens tested. Although there were minor differences in $CD25^+$ T cell responses between the different antigens tested, they were not significant.

Cytokine gene specific mRNA expression: A significant increase in recombinant antigen specific IFN-γ expression was detected in the immunized animals (P<0.01) in contrast to the control animals beginning at 6 wk APV (FIG. 9A). Though the expression levels peaked at 10 wk. APV, levels remained significantly higher in the immunized animals compared to the controls until 38 wk APV. In contrast, no significant differences were detected in IL-10 expression between the immunized and the control animals at any time point in our study, except for an overall increase in IL-10 expression levels at 26-38 wk APV in all three groups (FIG. 9B).

Recombinant antigen specific antibody responses: All four recombinant antigens tested in this study induced robust antibody responses in both vaccinated groups. The responses were significantly higher (P<0.01) in the vaccinated groups over the control group from six weeks APV through the entire experimental period (FIG. 10). No significant differences were detected in the antibody responses among the various recombinant antigens used.

Histopathology of tissues collected at necropsy: Histopathological examination of tissues collected from each animal at necropsy indicated that 75% of the unvaccinated control animals (Group III) had granulomas in at least one tissue, whereas group I and group I animals had granulomas in only 25 and 50% of animals respectively. Granulomas were found in a mesenteric lymph node and jejunum from 1 animal and the ileocecal lymph node of another animal in Group I. In contrast, granulomas in Groups II and III were located primarily in the ileum, ileocecal junction, or cecum, while the ileocecal lymph node was affected in 5 animals from these two groups. No granulomas were found in the duodenum of any animal and only 2 animals, one from Group I and 1 from Group III, had granulomas in the jejunum. Other affected tissues included the cecocolic junction and the hepatic lymph nodes in two of the unvaccinated control animals in Group III.

MAP burden in tissues following challenge: MAP burden in 23 tissues collected from each animal at necropsy was assessed by bacterial culture (FIG. 11). Among the vaccinated animals, only one animal in group I was culture positive with a very low CFU. In group II, although 5/8 animals were positive for MAP, the bacterial load was very low in four of the five animals (<5) from which MAP were isolated. In the unvaccinated group III, all nine animals were positive for MAP, with majority of the animals having at least 5 tissues positive for MAP with >300 CFU (too many to count).

As evidenced by the foregoing, in this Example, we assessed the protective efficacy of recombinant 85A, 85B, SOD and Map74F in a goat model. Since MAP is an intracellular organism, a Th1 response mediated by sensitized T cells, and in particular IFN-$\gamma$ secreting sensitized T cells, is believed to play a significant role in protection. Among the various tools used, measurement of lymphocyte proliferation response to the specific antigen tested is widely used to determine cellular immune responses. We demonstrate detection of recombinant antigen specific lymphocyte proliferation three weeks after the booster vaccination, which was significantly higher in the vaccinated groups compared to the controls following challenge, which indicates the induction of antigen specific cellular immunity.

IFN-$\gamma$ is one of the major cytokine genes activated in response to MAP infection in cattle. In addition, it is believed that major histocompatibility complex class I restricted $CD8^+$ T cells that produce cytokines such as IFN-$\gamma$ are required for resistance to other mycobacterial infections like *M. tuberculosis*. In this Example, Map74F mediated IFN-$\gamma$ response was detected after the booster vaccination and challenge. Without intending to be bound by any particular theory, it is considered that the enhanced levels of IFN-$\gamma$ could have played an important role in the protective immunity of the goats following challenge with live MAP by IFN-$\gamma$ mediated signaling of macrophages.

The results presented in this Example also show a higher $CD4^+$ and $CD8^+$T cell response in the immunized animals. Our results also support the contribution of $CD4^+$T cells to the peripheral IFN-$\gamma$ levels and proliferative responses following immunization with the recombinant antigens. CD25 is expressed by activated T-cells. Our results clearly indicate an expansion of activated T-cells in the vaccinated animals. Although the $\gamma\delta TCR^+$ cell population remained comparatively smaller than the $CD4^+$ and $CD8^+$T cells, they were significantly higher (P<0.05) in the immunized animals than the control animals. $CD4^+$T cell effector mechanisms are associated with the secretion of IFN-$\gamma$, which activates bactericidal activity in macrophages, lymphotoxin, perforin and granulysin. $CD8^+$ and $\gamma\delta^+$T cells also secrete granulysin. This is consistent with the results of our challenge experiments and support the protective efficacy of our recombinant antigens. The increased IFN-$\gamma$ mRNA expression levels clearly indicated that there was a definite antigen specific Th1 response in the immunized animals which was supported by the insignificant expression levels of the Th2 specific IL-10.

With the lymphoproliferative response, IFN-$\gamma$ response, $CD4^+$T and $CD8^+$T cell responses provide evidence for a significant Th1 response in the immunized groups. We analyzed the results of challenge experiments to assess the protective efficacy of the recombinant antigens in goats. In the absence of characteristic clinical signs, histopathology and bacterial burden of tissues collected at necropsy are considered to be the best standard in evaluating the protective efficacy of MAP vaccinations. We collected 23 tissues from each of the 25 animals and analyzed the tissues for histopathological lesions and MAP burden by culture. A significant reduction was observed in the number of animals and tissues with lesions in the group administered the recombinant antigens and DDA, indicating protective efficacy.

Isolation of MAP in culture is a more sensitive means of detecting MAP in tissues, as compared to either acid-fast staining or microscopic examination, especially during the very early phase of infection. However, the distribution of granulomatous lesions generally reflected the MAP culture results. MAP culture results presented in this Example clearly demonstrate the protective efficacy of the four recombinant antigens used. Protection was nearly complete when the antigens were given along with DDA. MAP was recovered from only one out of the eight animals of this group (I) and this animal had a significantly lower MAP load in the only one positive tissue, viz distal ileum. Administration of the antigens without the adjuvant showed protection, although the protective efficacy was comparatively less when the antigens were administered without the adjuvant. This can be observed from the culture results of group II animals which received antigens without the adjuvant. Although 5/8 animals were positive for MAP, the bacterial load was significantly lower in these animals compared to the group III control animals indicating the protective nature of the antigens even without the adjuvant. Significantly higher numbers of MAP were recovered from all the animals in the unvaccinated control group, which again demonstrates the protective efficacy of the antigens. Immunization of goats with the recombinant antigens resulted in a sustained antibody response for a prolonged period. The results presented in this Example therefore indicate that the recombinant antigens stimulated both cell mediated and humoral immune systems. After booster vaccination, a significant increase in antibody response was detected for all the recombinant antigens in both vaccine groups compared to the unvaccinated control group. The response trended higher in group I animals which received the antigens with the adjuvant, though not significantly. Early onset of CMI reactivity followed by seroconversion is a constant feature of mycobacterial infections of ruminants. However, our multicomponent subunits used in this Example imparted significant protection in terms of reduction of bacilli burden in target organs as compared to sham immunized goats.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A composition comprising a recombinant protein comprising from N-terminus to C-terminus:

i) a C-terminal fragment of Map3527 protein comprising amino acids 183-361 of SEQ ID NO:2;

ii) a Map1519 protein sequence comprising amino acids 1-460 of SEQ ID NO:3; and iii) an N-terminal fragment of Map3527 protein comprising amino acids 33-180 of SEQ ID NO:2.

2. The composition of claim 1, wherein the Map1519 protein sequence comprises the amino acid sequence of SEQ ID NO:3.

3. The composition of claim 1, wherein the polypeptide comprises the amino acid sequence of SEQ ID NO:1.

4. The composition of claim 1, wherein the composition further comprises an adjuvant.

5. The composition of claim 4, wherein the adjuvant is selected from the group consisting of monophosphoryl lipid A (MPL), dimethydioctadecyl ammonium bromide (DDA), and combinations thereof.

6. The composition of claim 1, further comprising a *Mycobacterium avium* subspecies *paratuberculosis* (MAP) protein, wherein the protein is selected from the group consisting of MAP protein 85A, MAP protein 85B, MAP protein superoxide dismutase (SOD), and combinations thereof.

7. A method for stimulating an immune response to *Mycobacterium avium* subspecies *paratuberculosis* (MAP) in a mammal comprising administering to the mammal the composition of claim 1.

8. The method of claim 7, wherein the composition further comprises an adjuvant.

9. The method of claim 8, wherein the adjuvant is selected from the group consisting of monophosphoryl lipid A (MPL) and dimethydioctadecyl ammonium bromide (DDA).

10. The method of claim 7, wherein the composition is administered to a ruminant.

11. The method of claim 10, wherein the ruminant is a bovine, a sheep, a goat, a deer or an elk.

12. The method of claim 11, wherein the ruminant is a bovine.

13. The method of claim 10, wherein the ruminant is not infected with MAP.

14. The method of claim 10, wherein the ruminant is infected with MAP.

15. The method of claim 12, wherein the bovine has Johne's Disease.

16. The method of claim 7, wherein the animal is pregnant.

17. The method of claim 7, wherein the composition further comprises a *Mycobacterium avium* subspecies *paratuberculosis* (MAP) protein, wherein the protein is selected from the group consisting of MAP protein 85A, MAP protein 85B, MAP protein SOD, and combinations thereof.

18. The method of claim 7, wherein the polypeptide of the composition comprises the sequence of SEQ ID NO:1.

* * * * *

SEQUENCE LISTING

<160> NUMBER OF SEQ ID NOS: 33

<210> SEQ ID NO 1
<211> LENGTH: 788
<212> TYPE: PRT
<213> ORGANISM: Artificial sequence
<220> FEATURE:
<223> OTHER INFORMATION: Map74F protein

<400> SEQUENCE: 1

```
Leu Asn Gln Ser Val Ser Ala Thr Asp Thr Leu Thr Gly Ala Gln Glu
 1               5                  10                  15

Asn Leu Gly Gly Leu Ile Gln Ala Asp Ala Pro Ile Lys Pro Gly Asp
            20                  25                  30

Ser Gly Gly Pro Met Val Asn Ser Ala Gly Gln Val Ile Gly Val Asp
        35                  40                  45

Thr Ala Thr Asp Ser Tyr Lys Met Ser Gly Gln Gly Phe Ala
 50                  55                  60

Ile Pro Ile Gly Arg Ala Met Ala Val Ala Asn Gln Ile Arg Ser Gly
 65                  70                  75                  80

Ala Gly Ser Asn Thr Val His Ile Gly Pro Thr Ala Phe Leu Gly Leu
                85                  90                  95

Gly Val Thr Asp Asn Asn Gly Asn Gly Ala Arg Val Gln Arg Val Val
               100                 105                 110

Asn Thr Gly Pro Ala Ala Ala Gly Ile Ala Pro Gly Asp Val Ile
               115                 120                 125

Thr Gly Val Asp Thr Val Pro Ile Asn Gly Ala Thr Ser Met Thr Glu
130                 135                 140

Val Leu Val Pro His His Pro Gly Asp Thr Ile Ala Val His Phe Arg
145                 150                 155                 160

Ser Val Asp Gly Gly Glu Arg Thr Ala Asn Ile Thr Leu Ala Glu Gly
               165                 170                 175

Pro Pro Ala Met Phe Tyr Gly Ala Phe Pro Pro Glu Phe Asn Ser Gly
               180                 185                 190

Arg Met Tyr Ser Gly Pro Gly Ala Gly Ser Phe Val Ala Ala Ala Thr
               195                 200                 205

Ala Trp Gln Asn Leu Ala Ala Glu Leu Gln Ser Ala Ala Ser Tyr
210                 215                 220

Ser Thr Val Leu Ser Gly Leu Thr Ala Gly Pro Trp Val Gly Pro Ser
225                 230                 235                 240

Ser Leu Ala Met Ala Ser Ala Ala Pro Tyr Val Ala Trp Met Gln
               245                 250                 255

Gln Thr Ala Ala Gln Ala Ala Glu Thr Ala Ala Gln Ala Thr Ala Ala
               260                 265                 270

Ala Thr Ala Tyr Glu Thr Ala Phe Ala Ala His Val Pro Ala Val
               275                 280                 285

Ile Thr Glu Asn Arg Ala Leu Leu Ala Gln Leu Val Ala Thr Asn Ile
               290                 295                 300

Phe Gly Gln Asn Thr Ala Ala Ile Ala Ala Asn Glu Ala Gln Tyr Gly
305                 310                 315                 320

Glu Phe Trp Ala Gln Asp Ala Thr Ala Met Asp Thr Tyr Phe Ala Ala
               325                 330                 335

Ser Ala Thr Ala Ala Asn Lys Leu Thr Glu Phe Gly Pro Ala Pro Lys
               340                 345                 350
```

-continued

```
Thr Thr Asn Glu Ala Ala Gln Pro Met Gln Ala Ala Val Ser Ser
        355                 360                 365

Ala Ala Ser Thr Pro Ala Ala Asn Val Ala Gln Thr Ala Ala Ser Ala
    370                 375                 380

Ala Ser Thr Thr Leu Pro Tyr Ser Gly Pro Phe Ser Gly Pro Ala Asn
385                 390                 395                 400

Leu Ala Tyr Leu Tyr Gln Thr Phe Met Thr Asn Leu Phe Asn Thr Val
                405                 410                 415

Pro Gly Gly Ala Ser Phe Tyr Thr Ser Met Tyr Asn Ala Val Lys Val
            420                 425                 430

Pro Leu Gly Leu Thr Thr Gln Phe Asn Asp Val Gly Leu Leu Val Asn
        435                 440                 445

Phe Pro Leu Ser Gln Trp Leu Lys Phe Ala Pro Pro Ile Gly Tyr Gly
    450                 455                 460

Ala Leu Pro Lys Asp Ala Leu Gly Ala Gly Leu Gly Ala Leu Gly Phe
465                 470                 475                 480

Gly Arg Gly Thr Leu Tyr Ser Ala Ile Ser Pro Val Ala Gly Met Gly
                485                 490                 495

Asn Ala Gly Thr Leu Val Gly Lys Leu Ser Ile Pro Pro Ser Trp Ala
            500                 505                 510

Thr Ala Thr Pro Ser Ile Arg Thr Val Ala Ala Ala Leu Ser Ala Ala
        515                 520                 525

Gly Ala Glu Ala Val Pro Ala Ala Ala Leu Gly Glu Gly Ser Leu Phe
    530                 535                 540

Ser Ser Met Gly Leu Ala Gly Met Leu Gly Ser Ala Val Gly Ser Gly
545                 550                 555                 560

Gly Pro Thr Met Val Arg Gly Val Arg Asn Arg Met Thr Ala Ile
                565                 570                 575

Lys Asp Leu Lys Asp Lys Gln Ser Pro Glu Gln Leu Lys Arg Leu Val
            580                 585                 590

Ala Gln Ile Ser Glu Gln Pro Glu Ser Val Gln His His Asn Val Asp
        595                 600                 605

Gln Glu Asn Leu Asp Ala Leu Leu Glu Gln Leu Ala Lys Lys Pro Gly
    610                 615                 620

Ile His Ala Val His Leu Lys Lys Gly Asp Lys Ser Lys Val Leu Gly
625                 630                 635                 640

Leu Ala Pro Ala Ser Ala Ala Pro Ser Gly Leu Ala Leu Asp Arg Phe
                645                 650                 655

Ala Asp Arg Pro Leu Ala Pro Ile Asp Pro Ser Ala Met Val Gly Gln
            660                 665                 670

Val Gly Pro Gln Val Val Asn Ile Asp Thr Lys Phe Gly Tyr Asn Asn
        675                 680                 685

Ala Val Gly Ala Gly Thr Gly Ile Val Ile Asp Pro Asn Gly Val Val
    690                 695                 700

Leu Thr Asn Asn His Val Ile Ser Gly Ala Thr Glu Ile Ser Ala Phe
705                 710                 715                 720

Asp Val Gly Asn Gly Gln Thr Tyr Ala Val Asp Val Gly Tyr Asp
                725                 730                 735

Arg Thr Gln Asp Ile Ala Val Leu Gln Leu Arg Gly Ala Ala Gly Leu
            740                 745                 750

Pro Thr Ala Thr Ile Gly Gly Glu Ala Thr Val Gly Glu Pro Ile Val
        755                 760                 765
```

```
Ala Leu Gly Asn Val Gly Gly Gln Gly Gly Thr Pro Asn Ala Val Ala
770                 775                 780

Gly Lys Val Ala
785

<210> SEQ ID NO 2
<211> LENGTH: 361
<212> TYPE: PRT
<213> ORGANISM: MYCOBACTERIUM AVIUM SUBSPECIES PARATUBERCULOSIS

<400> SEQUENCE: 2

Met Ser Lys Ser His His His Arg Ser Val Trp Trp Ser Trp Leu Val
1               5                   10                  15

Gly Val Leu Thr Val Val Gly Leu Gly Leu Gly Leu Gly Ser Gly Val
                20                  25                  30

Gly Leu Ala Pro Ala Ser Ala Ala Pro Ser Gly Leu Ala Leu Asp Arg
            35                  40                  45

Phe Ala Asp Arg Pro Leu Ala Pro Ile Asp Pro Ser Ala Met Val Gly
    50                  55                  60

Gln Val Gly Pro Gln Val Val Asn Ile Asp Thr Lys Phe Gly Tyr Asn
65                  70                  75                  80

Asn Ala Val Gly Ala Gly Thr Gly Ile Val Ile Asp Pro Asn Gly Val
                85                  90                  95

Val Leu Thr Asn Asn His Val Ile Ser Gly Ala Thr Glu Ile Ser Ala
                100                 105                 110

Phe Asp Val Gly Asn Gly Gln Thr Tyr Ala Val Asp Val Val Gly Tyr
            115                 120                 125

Asp Arg Thr Gln Asp Ile Ala Val Leu Gln Leu Arg Gly Ala Ala Gly
    130                 135                 140

Leu Pro Thr Ala Thr Ile Gly Gly Glu Ala Thr Val Gly Glu Pro Ile
145                 150                 155                 160

Val Ala Leu Gly Asn Val Gly Gly Gln Gly Gly Thr Pro Asn Ala Val
                165                 170                 175

Ala Gly Lys Val Val Ala Leu Asn Gln Ser Val Ser Ala Thr Asp Thr
            180                 185                 190

Leu Thr Gly Ala Gln Glu Asn Leu Gly Gly Leu Ile Gln Ala Asp Ala
    195                 200                 205

Pro Ile Lys Pro Gly Asp Ser Gly Gly Pro Met Val Asn Ser Ala Gly
    210                 215                 220

Gln Val Ile Gly Val Asp Thr Ala Ala Thr Asp Ser Tyr Lys Met Ser
225                 230                 235                 240

Gly Gly Gln Gly Phe Ala Ile Pro Ile Gly Arg Ala Met Ala Val Ala
                245                 250                 255

Asn Gln Ile Arg Ser Gly Ala Gly Ser Asn Thr Val His Ile Gly Pro
            260                 265                 270

Thr Ala Phe Leu Gly Leu Gly Val Thr Asp Asn Asn Gly Asn Gly Ala
    275                 280                 285

Arg Val Gln Arg Val Val Asn Thr Gly Pro Ala Ala Ala Gly Ile
    290                 295                 300

Ala Pro Gly Asp Val Ile Thr Gly Val Asp Thr Val Pro Ile Asn Gly
305                 310                 315                 320

Ala Thr Ser Met Thr Glu Val Leu Val Pro His His Pro Gly Asp Thr
                325                 330                 335

Ile Ala Val His Phe Arg Ser Val Asp Gly Gly Glu Arg Thr Ala Asn
            340                 345                 350
```

```
Ile Thr Leu Ala Glu Gly Pro Pro Ala
        355                 360
```

<210> SEQ ID NO 3
<211> LENGTH: 467
<212> TYPE: PRT
<213> ORGANISM: MYCOBACTERIUM AVIUM SUBSPECIES PARATUBERCULOSIS

<400> SEQUENCE: 3

```
Met Phe Tyr Gly Ala Phe Pro Pro Glu Phe Asn Ser Gly Arg Met Tyr
1               5                   10                  15

Ser Gly Pro Gly Ala Gly Ser Phe Val Ala Ala Ala Thr Ala Trp Gln
            20                  25                  30

Asn Leu Ala Ala Glu Leu Gln Ser Ala Ala Ala Ser Tyr Ser Thr Val
        35                  40                  45

Leu Ser Gly Leu Thr Ala Gly Pro Trp Val Gly Pro Ser Ser Leu Ala
    50                  55                  60

Met Ala Ser Ala Ala Ala Pro Tyr Val Ala Trp Met Gln Gln Thr Ala
65                  70                  75                  80

Ala Gln Ala Ala Glu Thr Ala Ala Gln Ala Thr Ala Ala Ala Thr Ala
                85                  90                  95

Tyr Glu Thr Ala Phe Ala Ala His Val Pro Pro Ala Val Ile Thr Glu
            100                 105                 110

Asn Arg Ala Leu Leu Ala Gln Leu Val Ala Thr Asn Ile Phe Gly Gln
        115                 120                 125

Asn Thr Ala Ala Ile Ala Ala Asn Glu Ala Gln Tyr Gly Glu Phe Trp
    130                 135                 140

Ala Gln Asp Ala Thr Ala Met Asp Thr Tyr Phe Ala Ala Ser Ala Thr
145                 150                 155                 160

Ala Ala Asn Lys Leu Thr Glu Phe Gly Pro Ala Pro Lys Thr Thr Asn
                165                 170                 175

Glu Ala Ala Gln Pro Met Gln Ala Ala Val Ser Ser Ala Ala Ser
            180                 185                 190

Thr Pro Ala Ala Asn Val Ala Gln Thr Ala Ser Ala Ser Thr
        195                 200                 205

Thr Leu Pro Tyr Ser Gly Pro Phe Ser Gly Pro Ala Asn Leu Ala Tyr
    210                 215                 220

Leu Tyr Gln Thr Phe Met Thr Asn Leu Phe Asn Thr Val Pro Gly Gly
225                 230                 235                 240

Ala Ser Phe Tyr Thr Ser Met Tyr Asn Ala Val Lys Val Pro Leu Gly
                245                 250                 255

Leu Thr Thr Gln Phe Asn Asp Val Gly Leu Leu Val Asn Phe Pro Leu
            260                 265                 270

Ser Gln Trp Leu Lys Phe Ala Pro Pro Ile Gly Tyr Gly Ala Leu Pro
        275                 280                 285

Lys Asp Ala Leu Gly Ala Gly Leu Gly Ala Leu Gly Phe Gly Arg Gly
    290                 295                 300

Thr Leu Tyr Ser Ala Ile Ser Pro Val Ala Gly Met Gly Asn Ala Gly
305                 310                 315                 320

Thr Leu Val Gly Lys Leu Ser Ile Pro Pro Ser Trp Ala Thr Ala Thr
                325                 330                 335

Pro Ser Ile Arg Thr Val Ala Ala Ala Leu Ser Ala Ala Gly Ala Glu
            340                 345                 350

Ala Val Pro Ala Ala Ala Leu Gly Glu Gly Ser Leu Phe Ser Ser Met
```

355                 360                 365
Gly Leu Ala Gly Met Leu Gly Ser Ala Val Ser Gly Gly Pro Thr
    370                 375                 380

Met Val Arg Gly Val Arg Asn Arg Met Thr Ala Ile Lys Asp Leu
385                 390                 395                 400

Lys Asp Lys Gln Ser Pro Glu Gln Leu Lys Arg Leu Val Ala Gln Ile
                405                 410                 415

Ser Glu Gln Pro Glu Ser Val Gln His His Asn Val Asp Gln Glu Asn
                420                 425                 430

Leu Asp Ala Leu Leu Glu Gln Leu Ala Lys Lys Pro Gly Ile His Ala
            435                 440                 445

Val His Leu Lys Lys Gly Asp Lys Ser Lys Val Leu Pro Ala Asp Ala
        450                 455                 460

Gln Leu Gly
465

<210> SEQ ID NO 4
<211> LENGTH: 44
<212> TYPE: DNA
<213> ORGANISM: Artificial sequence
<220> FEATURE:
<223> OTHER INFORMATION: PCR amplification primer

<400> SEQUENCE: 4
tacatatgca tcatcatcat catcatctca accagagcgt ctcg         44

<210> SEQ ID NO 5
<211> LENGTH: 27
<212> TYPE: DNA
<213> ORGANISM: Artificial sequence
<220> FEATURE:
<223> OTHER INFORMATION: PCR primer

<400> SEQUENCE: 5
tagaattcgg ccggcggccc ctccgcc                            27

<210> SEQ ID NO 6
<211> LENGTH: 31
<212> TYPE: DNA
<213> ORGANISM: Artificial sequence
<220> FEATURE:
<223> OTHER INFORMATION: PCR primer

<400> SEQUENCE: 6
ctaatcgaat tcatgttcta tggggccttt c                       31

<210> SEQ ID NO 7
<211> LENGTH: 29
<212> TYPE: DNA
<213> ORGANISM: Artificial sequence
<220> FEATURE:
<223> OTHER INFORMATION: PCR primer

<400> SEQUENCE: 7
taatcgatat ccaggacctt ggacttgtc                          29

<210> SEQ ID NO 8
<211> LENGTH: 26
<212> TYPE: DNA
<213> ORGANISM: Artificial sequence
<220> FEATURE:
<223> OTHER INFORMATION: PCR primer

```
<400> SEQUENCE: 8
atgatatcgg gctggcgccg gcgtcc                                    26

<210> SEQ ID NO 9
<211> LENGTH: 26
<212> TYPE: DNA
<213> ORGANISM: Artificial sequence
<220> FEATURE:
<223> OTHER INFORMATION: PCR primer

<400> SEQUENCE: 9
atctcgagtc acgcgacctt gccggc                                    26

<210> SEQ ID NO 10
<211> LENGTH: 23
<212> TYPE: DNA
<213> ORGANISM: Mouse

<400> SEQUENCE: 10
cctgagcagg atggagaatt aca                                       23

<210> SEQ ID NO 11
<211> LENGTH: 19
<212> TYPE: DNA
<213> ORGANISM: Mouse

<400> SEQUENCE: 11
tccagaacat gccgcagag                                            19

<210> SEQ ID NO 12
<211> LENGTH: 25
<212> TYPE: DNA
<213> ORGANISM: mouse

<400> SEQUENCE: 12
cccaagcagg ccacagaatt gaaag                                     25

<210> SEQ ID NO 13
<211> LENGTH: 20
<212> TYPE: DNA
<213> ORGANISM: mouse

<400> SEQUENCE: 13
ggaagcacgg cagcagaata                                           20

<210> SEQ ID NO 14
<211> LENGTH: 24
<212> TYPE: DNA
<213> ORGANISM: mouse

<400> SEQUENCE: 14
aacttgaggg agaagtagga atgg                                      24

<210> SEQ ID NO 15
<211> LENGTH: 24
<212> TYPE: DNA
<213> ORGANISM: mouse

<400> SEQUENCE: 15
catcatcaaa ccagacccgc ccaa                                      24

<210> SEQ ID NO 16
<211> LENGTH: 25
```

<210> SEQ ID NO 16
<211> LENGTH: 25 (implied)
<212> TYPE: DNA
<213> ORGANISM: mouse

<400> SEQUENCE: 16
catcttctca aaattcgagt gacaa                                            25

<210> SEQ ID NO 17
<211> LENGTH: 23
<212> TYPE: DNA
<213> ORGANISM: mouse

<400> SEQUENCE: 17
tgggagtaga caaggtacaa ccc                                              23

<210> SEQ ID NO 18
<211> LENGTH: 26
<212> TYPE: DNA
<213> ORGANISM: mouse

<400> SEQUENCE: 18
cacgtcgtag caaaccacca agtgga                                           26

<210> SEQ ID NO 19
<211> LENGTH: 24
<212> TYPE: DNA
<213> ORGANISM: mouse

<400> SEQUENCE: 19
tcaagtggca tagatgtgga agaa                                             24

<210> SEQ ID NO 20
<211> LENGTH: 21
<212> TYPE: DNA
<213> ORGANISM: mouse

<400> SEQUENCE: 20
tggctctgca ggattttcat g                                                21

<210> SEQ ID NO 21
<211> LENGTH: 27
<212> TYPE: DNA
<213> ORGANISM: mouse

<400> SEQUENCE: 21
tcaccatcct tttgccagtt cctccag                                          27

<210> SEQ ID NO 22
<211> LENGTH: 19
<212> TYPE: DNA
<213> ORGANISM: mouse

<400> SEQUENCE: 22
tcaccaccat ggagaaggc                                                   19

<210> SEQ ID NO 23
<211> LENGTH: 20
<212> TYPE: DNA
<213> ORGANISM: mouse

<400> SEQUENCE: 23
gctaagcagt tggtggtgca                                                  20

<210> SEQ ID NO 24

```
<211> LENGTH: 25
<212> TYPE: DNA
<213> ORGANISM: mouse

<400> SEQUENCE: 24
atgcccccat gtttgtgatg ggtgt                                         25

<210> SEQ ID NO 25
<211> LENGTH: 21
<212> TYPE: DNA
<213> ORGANISM: Bovine

<400> SEQUENCE: 25
caaattccgg tggatgatct g                                             21

<210> SEQ ID NO 26
<211> LENGTH: 22
<212> TYPE: DNA
<213> ORGANISM: Bovine

<400> SEQUENCE: 26
gcgacaggtc attcatcacc tt                                            22

<210> SEQ ID NO 27
<211> LENGTH: 28
<212> TYPE: DNA
<213> ORGANISM: bovine

<400> SEQUENCE: 27
atccagcgca aagccataaa tgaactca                                      28

<210> SEQ ID NO 28
<211> LENGTH: 23
<212> TYPE: DNA
<213> ORGANISM: bovine

<400> SEQUENCE: 28
ccaggatggt gactcgacta gac                                           23

<210> SEQ ID NO 29
<211> LENGTH: 20
<212> TYPE: DNA
<213> ORGANISM: bovine

<400> SEQUENCE: 29
tggctctgct ctcccagaac                                               20

<210> SEQ ID NO 30
<211> LENGTH: 28
<212> TYPE: DNA
<213> ORGANISM: bovine

<400> SEQUENCE: 30
ccgacataaa cctctgaaat ccgaccca                                      28

<210> SEQ ID NO 31
<211> LENGTH: 18
<212> TYPE: DNA
<213> ORGANISM: bovine

<400> SEQUENCE: 31 gccctctga accccaaa                                                  18
```

-continued

```
<210> SEQ ID NO 32
<211> LENGTH: 23
<212> TYPE: DNA
<213> ORGANISM: bovine

<400> SEQUENCE: 32
gcaggagtgt tgaaagtctc gaa                                              23

<210> SEQ ID NO 33
<211> LENGTH: 27
<212> TYPE: DNA
<213> ORGANISM: bovine

<400> SEQUENCE: 33
ccaaccgtga gaagatgacc cagatca                                          27
```